United States Patent
Fiorini-Puybaret et al.

(10) Patent No.: US 11,707,428 B2
(45) Date of Patent: Jul. 25, 2023

(54) **DYE COMPOSITION COMPRISING A COMBINATION OF TWO PLANT EXTRACTS OF *LAWSONIA INERMIS***

(71) Applicant: PIERRE FABRE DERMO-COSMETIQUE, Boulogne-Billancourt (FR)

(72) Inventors: Christel Fiorini-Puybaret, Toulouse (FR); Philippe Joulia, Villenouvelle (FR)

(73) Assignee: PIERRE FABRE DERMO-COSMETIQUE, Boulogne-Billancourt (FR)

(*) Notice: Subject to any disclaimer, the term of this patent is extended or adjusted under 35 U.S.C. 154(b) by 0 days.

(21) Appl. No.: 17/608,432

(22) PCT Filed: Jun. 12, 2020

(86) PCT No.: PCT/EP2020/066331
§ 371 (c)(1),
(2) Date: Nov. 2, 2021

(87) PCT Pub. No.: WO2020/249748
PCT Pub. Date: Dec. 17, 2020

(65) Prior Publication Data
US 2022/0192971 A1  Jun. 23, 2022

(30) Foreign Application Priority Data
Jun. 12, 2019 (FR) ........................ 1906266

(51) Int. Cl.
*A61Q 5/10* (2006.01)
*A61K 8/9789* (2017.01)
(Continued)

(52) U.S. Cl.
CPC ............ *A61K 8/9789* (2017.08); *A61Q 5/065* (2013.01); *C09B 61/00* (2013.01); *C09B 67/0033* (2013.01); *A61K 2800/43* (2013.01)

(58) Field of Classification Search
CPC .. A61K 8/9789; A61K 2800/43; A61K 8/355; A61K 2800/805; A61Q 5/065;
(Continued)

(56) References Cited

U.S. PATENT DOCUMENTS

2007/0251024 A1* 11/2007 Greaves ................. A61Q 5/065
8/405
2020/0330365 A1* 10/2020 Fiorini Puybaret .. A61K 36/185

FOREIGN PATENT DOCUMENTS

FR    2 473 310 A1    7/1981
FR    3 004 943 A1    10/2014
(Continued)

OTHER PUBLICATIONS

English translation of the International Search Report and Written Opinion of the International Searching Authority for International Application No. PCT/EP2020/066331, dated Sep. 23, 2020.
(Continued)

*Primary Examiner* — Eisa B Elhilo
(74) *Attorney, Agent, or Firm* — Birch, Stewart, Kolasch & Birch, LLP

(57) ABSTRACT

The disclosure relates to a dye composition comprising a combination of two extracts of *Lawsonia inermis* and a method for preparing thereof. The disclosure also relates to the cosmetic use of said composition for dyeing keratin fibers. Finally, the disclosure relates to a cosmetic method for dyeing keratin fibers comprising the application of such a composition.

17 Claims, 10 Drawing Sheets

(51) Int. Cl.
  *A61Q 5/06* (2006.01)
  *C09B 61/00* (2006.01)
  *C09B 67/22* (2006.01)

(58) Field of Classification Search
  CPC ...... A61Q 5/10; C09B 61/00; C09B 67/0033; C09B 67/0034
  USPC .......................................................... 8/405
  See application file for complete search history.

(56) References Cited

FOREIGN PATENT DOCUMENTS

| FR | 3 072 879 A1 | 5/2019 | | |
| FR | 3074690 A1 * | 6/2019 | ............... | A61K 8/97 |
| WO | WO 2018/162760 A1 | 9/2018 | | |
| WO | WO 2019/115651 A1 * | 6/2019 | ............... | A61Q 5/10 |

OTHER PUBLICATIONS

French Preliminary Search Report and Written Opinion for French Application No. 1906266, dated Feb. 14, 2020.

Gallo et al., "Henna through the centuries: a quick HPTLC anaylsis proposal to check henna identity," Rev Bras Farmacogn, vol. 24, 2014, pp. 133-140.

Huh et al., "A cell-based system for screening hair growth-promoting agents," Arch Dermatol Res, vol. 301, 2009 (Published online Mar. 11, 2009), pp. 381-385.

Nichols et al., "Skin photoprotection by natural polyphenols: Anti-inflammatory, anti-oxidant and DNA repair mechanisms," Arch Dermatol Res., vol. 302, No. 2, Mar. 2010, pp. 1-19.

Saewan et al., "Photoprotection of natural flavonoids," Journal of Applied Pharmaceutical Science, vol. 3, No. 9, Sep. 2013, pp. 129-141.

* cited by examiner

DYE COMPOSITION COMPRISING A COMBINATION OF TWO PLANT EXTRACTS OF *LAWSONIA INERMIS*

TECHNICAL FIELD

The invention relates to a dye composition comprising a combination of two natural dyeing agents, in particular of two extracts of *Lawsonia inermis*. The invention also relates to the cosmetic use of said composition for dyeing keratin fibers. Finally, the invention relates to a cosmetic method for dyeing keratin fibers comprising the application of such a composition.

TECHNICAL BACKGROUND

Methods for dyeing hair include oxidation, or permanent, dye. This chemical dyeing method implements one or more oxidation dye precursors, usually one or more oxidation bases optionally combined with one or more couplers.

These oxidation bases are colorless or faintly colored compounds that, combined with oxidizing products, allow access, through an oxidative condensation process, to the colored species that remain trapped inside the hair fiber.

However, oxidation dyes are known to cause skin problems. Moreover, it has been demonstrated that oxidation dyes are endocrine disruptors that negatively affect an ecosystem, and also that they may cause cancers, allergies, and the like.

Colored molecules and dyes may also be natural compounds derived from plants or trees. *Lawsonia inermis*, commonly called henna, belongs to the Lythraceae family. This shrub, which can reach a height of 6 meters, grows naturally in the tropical and subtropical regions of Africa and Asia, notably. It has a gray bark, dense branching, and quadrangular and thorny branches on the oldest ones. Its leaves grow opposite each other and are simple and whole. The scented white or red flowers are grouped in large pyramidal panicles of 25 cm long.

Henna leaves, which produce red and orange tints, have been used for more than 5000 years for dyeing hair and skin, or even textile dyeing.

Their dye properties are due to lawsone (2-hydroxy-1,4-naphthoquinone), which reacts with the keratin present in the skin or nails by a Michael addition.

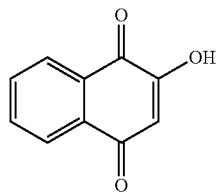 [SMILES: O=C1C=C(O)C(=O)c2ccccc21]

However, it is difficult with henna alone to consider all the tinctorial shades of the hair range, from blond to dark blond or even black.

Other plants have been described as sources of extract or powder for dye, notably for dyeing hair or other keratinous materials. However, each plant leads to a particular color. Moreover, the combination of several plant extracts has the risk of inducing undesirable interactions among pigments or extract compounds. These interactions may be tinctorial, such as dye accidents, or dermatological side effects.

Also, it is difficult to provide a shade ranging from blond to dark blond or even black, and covering the entire tinctorial range, notably hair, using only plant extracts or powders with no incompatibilities, therefore limited in number, and by using a henna extract as base.

It is even more difficult to use a single plant source to obtain a dye composition permitting obtaining a broad dye range from blond to dark blond. This would also be highly desirable and permit simplifying procurement of plant material, rationalizing production of extracts and dye composition on the industrial scale.

In the field of hair dye, we talk about tone-on-tone dye or permanent or semi-permanent dye, the latter generally using more hydrogen peroxide and alkaline chemical agents.

Tone-on-tone dye is generally used to enhance or intensify the natural color of the hair, give it highlights, and a great deal of shine.

Therefore, it is chosen most of the time in the same color tones as the natural hair or darker. In the field of permanent or semi-permanent hair dye, it is desirable for the dye to resist shampooing.

When henna is used, this gives a copper or red color to the hair through the use of a more or less standardized extract. This being the case, as indicated above, obtaining a broad color chart with a dye composition based only on henna has never been described.

The invention relates to both tone-on-tone dye and permanent dye.

Consequently, there is a real need to develop hair dyes from natural products, in particular henna, covering the entire range of hair color, in particular for a tone-on-tone approach or for a permanent dye approach that permits covering white hair, while limiting the number of plant extracts to simplify formulation and avoid interactions and incompatibilities. In particular, there is a need to develop and provide dye compositions based on a single plant source covering the tinctorial range.

In particular, the invention aims to provide a dye composition:
  that is natural, free of animal products, i.e., based on dye active ingredients from plants, microorganisms or microalgae;
  with a short exposure time, advantageously less than an hour for dyeing hair;
  preferably in a single application, including for dyeing hair;
  preferably organic and vegan;
  permitting good color retention, including after several washes, including after 10 shampoos, advantageously 15 shampoos, for a hair dye.

A permanent hair dye that avoids the use of hydrogen peroxide and alkaline chemical agents is also sought.

Moreover, it is desirable to be able to achieve all the colors sought.

The inventors of the present invention thus have developed a dye composition based on the combination of two henna extracts while allowing a broad range of colors to be attained. In particular, for use in the hair field, the composition covers the entire range of shades from black to very light blond.

The inventors of the present invention have thus developed a dye composition based on the combination of two henna extracts and allowing the set objective to be attained, including a broad range of colors. In particular, for use in the hair field, the composition covers a very broad range of shades while using a single source of plant raw material.

SUMMARY OF THE INVENTION

The invention relates to a method for preparing a dye composition, in particular for preparing a cosmetic dye composition for dyeing keratin fibers, comprising the following steps:
Providing an extract A of the aerial parts of *Lawsonia inermis* containing from 7 to 60% by weight of lawsone relative to the total weight of the dry extract, wherein the lawsone results notably from enzymatic hydrolysis of glycosylated lawsone derivatives, such as hennosides; and
Providing an extract B of the aerial parts of *Lawsonia inermis* containing less than 0.6% by weight of lawsone, at least 15% by weight of phenol compounds and at least 60% by weight of saccharide compounds, including polysaccharides, relative to the total weight of the dry extract;
Mixing extract A and extract B;
Obtaining a dye composition.

The invention further relates to a dye composition obtained by the disclosed method and the use thereof for dyeing keratin fibers.

The invention also relates to method for dyeing human keratin fibers comprising the following steps:
a) Providing a dye composition as disclosed herein in powder form,
b) Preparing an aqueous composition, by adding to the powder of step a) an aqueous composition, notably water, at a temperature between 20° C. and 98° C. and mixing,
c) Applying onto keratin fibers, optionally while heating the fibers thus treated,
d) Rinsing,
e) Optionally, repeating steps c) and d).

Further aspects of the invention are as recited in the claims and/or described herein below.

DETAILED DESCRIPTION

The present invention relates to a method for preparing a dye composition, in particular for preparing a cosmetic dye composition for dyeing keratin fibers, comprising the following steps:
Providing an extract A of the aerial parts of *Lawsonia inermis* containing from 7 to 60% by weight of lawsone relative to the total weight of the dry extract, wherein the lawsone results notably from enzymatic hydrolysis of glycosylated lawsone derivatives, such as hennosides; and
Providing an extract B of the aerial parts of *Lawsonia inermis* containing less than 0.6% by weight of lawsone, at least 15% by weight of phenol compounds and at least 60%, in particular from 60% to 80%, by weight of saccharide compounds, including polysaccharides (e.g. mucilages), relative to the total weight of the dry extract;
Mixing extract A and extract B;
Obtaining a dye composition.

The invention also relates to the dye composition obtained by the method disclosed herein.

Definitions

The following terms, when used herein, shall have the following meaning.

"Plant extract" means a product extracted from a plant, whether it is the whole plant, the aerial parts, the underground parts, the flowers or the fruits, including dried fruits. The extraction can consist of a mere pressing or involve the use of an extraction solvent. The solvent is advantageously water, a hydroalcoholic solvent or an alcoholic solvent, even if other types of solvents can be considered in particular for extract A of henna.

The present invention is part of a desire to set up synthesis pathways that are greener and that allow claiming that the active ingredients thus obtained are natural. Therefore, the solvent(s) used in the present invention will preferably be natural solvents and/or of natural origin from renewable resources, as opposed to fossil resources, these solvents advantageously being obtainable by processes that respect the environment. The extract thus obtained will be a natural extract and/or of natural origin, coming from renewable resources, as opposed to fossil resources.

"Dry extract" means an extract with no extraction solvent or medium, or containing them only in insignificant traces. Such a dry extract thus contains only the material coming from the plant, in particular from *Lawsonia inermis* for henna extract A.

"Standardized extract" means an extract having a chosen content for at least one of the dye components of the plant extract. A standardized extract is typically obtained by adding an inert carrier to the plant extract in an amount that may vary from one batch to another.

Said "carrier" must be inert vis-à-vis the extract and its components: it does not interact with the extract nor its components, more particularly with lawsone, contributes to its protection and allows to standardize the final content of the active extract or molecule.

The carrier may be chosen from among propanediol, pentanediol, glycerine, propylene glycol, methyl THF and amylic alcohol.

The carrier may also be chosen from among sugars and polysaccharide derivatives, such as fructose, glucose, saccharose, maltodextrins, cellulose derivatives, starch (e.g. maize, wheat or rice starch), agar-agar, gums, mucilages; and polyols such as mannitol, sorbitol, xylitol, etc. In particular, the support is selected from fructose, maltodextrins and starch, in particular rice starch.

The carrier is preferably a natural carrier and/or of natural origin from renewable resources, as opposed to fossil resources, these carriers advantageously being obtainable by processes that respect the environment.

"Dry standardized extract" means a standardized extract free of extraction solvent, or containing it only in non-significant trace amount.

«Powder» means a product in the form of fine particles with an average particle size of between 0.1 µm and 250 µm, in particular between 1 µm and 250 µm. These fine particles may be obtained by grinding. The grinding can be carried out by any suitable means allowing a size reduction and obtention of fine particles as mentioned above.

Advantageously, a powder according to the invention is a dry and pulverulent product whose moisture is negligible. A powder according to the invention is water-soluble or easily water-dispersible, i.e. it can be used to obtain an aqueous or hydroalcoholic liquid composition containing from 20 to 60% by weight of dry matter, more particularly from 30 to 50% by weight of dry matter, more particularly about 40% of dry matter. The dry matter thus represents the powder.

"Plant powder" means a pure natural product originating from a plant, whether it is the whole plant, the aerial parts, the underground parts, the flowers or the fruits, including dried fruits, which are reduced to powders by grinding or any other mechanical means.

"Aerial parts" means the parts of the plant above the ground, for example, the leaves, petioles, flowers, seeds and branches, in particular leaves, branches and petioles, or a mix thereof, preferably leaves, branches or a mix thereof.

"Glycosylated lawsone derivatives", also called lawsone glycosides or heterosides, means any compound of general formula (I) below:

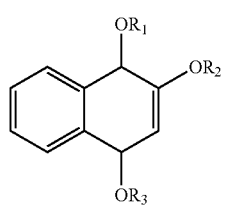

wherein $R_1$, $R_2$ and $R_3$ represent, independently of one another, H or a sugar, such as glucose, at least one of $R_1$ to $R_3$ being different from H, for which hydrolysis of the glycoside bond(s) leads to the formation of aglycone which undergoes an autooxidation reaction to form lawsone.

In particular, hennosides A, B and C are glycosylated lawsone derivatives.

"Enzymatic hydrolysis" refers to a hydrolysis reaction catalyzed by an enzyme, which can be an endogenous *Lawsonia inermis* enzyme or an enzyme from an exogenous source, preferably an endogenous *Lawsonia inermis* enzyme, it being understood that said enzyme is a glucosidase, such as a β-glucosidase [Gallo et al.], whose action leads to breaking the glucoside bonds of the glycosylated lawsone derivatives.

The terms "stable over time" with reference to a *Lawsonia inermis* extract as disclosed herein means that the quantity of lawsone initially present in the extract does not decrease by more than 50%, advantageously not more than 40%, in particular not more than 30%, advantageously not more than 20%, notably not more than 15%, advantageously not more than 10% in 1 month at room temperature (15° C.-25° C.), with a relative humidity (RH) of 60%, and protected from light. The room temperature values are those defined in the European Pharmacopoeia.

The stability of an extract A as disclosed herein may also be evaluated under so-called accelerated stability conditions. These conditions are a temperature of 40° C. (±2) and an RH of 75% (±5). The lawsone content of an extract is "stable over time" under accelerated stability conditions if the quantity of lawsone initially present in the extract does not decrease by more than 50%, advantageously not more than 40%, preferably not more than 30%, particularly not more than 20%, notably not more than 15%, advantageously not more than 10% in 1 month.

"Neutral pH" means a pH ranging from 6.5 to 7.5, particularly about 7.

"Acidic pH" means a pH below 7, advantageously below 6.5, more advantageously below 6.

"Weakly polar" means a solvent characterized by a dipole moment less than 2.0 D.

"Alcohol" means a compound of formula $R_4$—OH in which $R_4$ is a hydrocarbon group, in particular a ($C_1$-$C_6$) alkyl group or a $C_4$-$C_{12}$ hydrocarbon group. Alcohols comprising a ($C_1$-$C_6$)alkyl group are referred herein as «$C_1$-$C_6$ alcohols». Alcohol comprising a $C_4$-$C_{12}$ hydrocarbon group are referred herein as «$C_4$-$C_{12}$ alcohols».

"Chlorinated solvent" means an alkane, i.e. a saturated hydrocarbon, containing from 1 to 6 carbon atoms, in particular from 1 to 3 carbon atoms, of which a part or all of the hydrogen atoms are replaced by chlorine atoms.

"Ketone" means a compound of formula $R_5$—CO—$R_6$, in which $R_5$ and $R_6$ are identical or different ($C_1$-$C_6$) alkyl groups.

"Ether" means a compound of formula $R_7$—O—$R_8$, in which $R_7$ and $R_8$ are identical or different ($C_1$-$C_6$) alkyl groups.

"Ester" means a compound of formula $R_9$—COO—$R_{10}$ in which $R_9$ and $R_{10}$ are ($C_1$-$C_6$) alkyl groups that may be identical or different. The ester may, in particular, be an acetate, i.e., a $CH_3COO$—$R_{10}$ compound.

"($C_1$-$C_6$) alkyl" group means a saturated, linear or branched hydrocarbon chain, advantageously comprising 1 to 6, preferably 1 to 4 carbon atoms. Examples include the following groups: methyl, ethyl, propyl, isopropyl, butyl, isobutyl, sec-butyl, tert-butyl, pentyl or hexyl.

"$C_4$-$C_{12}$ hydrocarbon chain" designates a linear or branched, saturated or unsaturated, preferably saturated, hydrocarbon chain comprising from 4 to 12 carbon atoms, preferably from 4 to 8 carbon atoms. Examples of "$C_4$-$C_{12}$ hydrocarbon chain" include, but are not limited to, butyl, pentyl, hexyl, heptyl, octyl, nonyl, decyl, undecyl, dodecyl, including any of their positional isomers.

"Saturated or unsaturated hydrocarbon" means a compound made up uniquely of hydrogen and carbon atoms.

"Keratin fibers" means the keratin present in the epidermis and integuments, such as skin, hair, eyelashes, eyebrows, in particular hairs.

"cosmetically-acceptable", means that it is useful in the preparation of a cosmetic composition, and generally safe, non-toxic and neither biologically nor otherwise undesirable, and that is acceptable for a cosmetic use, notably by topical application on keratin fibers, in particular hair and scalp.

"Cosmetically-acceptable excipient" means an excipient containing ingredients suitable for formulating cosmetic compositions, such as cream, lotion, shampoo, emulsion or any formulation suitable for application on keratin fibers, in particular on hair.

Henna Extract A

The dye composition of the present invention comprises at least one particular Henna extract, referred herein as "extract A".

This extract A is characterized by a high lawsone content.

Thus, the extract A contains from 7 to 60% by weight of lawsone relative to the total weight of the dry extract. This lawsone content is advantageously stable over time, even under accelerated stability conditions.

In some embodiments, the lawsone content of an extract A does not decrease by more than 50%, advantageously not more than 40%, particularly not more than 30%, advantageously not more than 20%, more advantageously not more than 10%, in 3 months at room temperature (15° C.-25° C.), with a relative humidity (RH) of 60%, and protected from light. Advantageously, the lawsone content of an extract A does not decrease by more than 50%, advantageously not more than 40%, particularly not more than 30%, advantageously not more than 20%, more advantageously not more than 10%, in 6 months at room temperature (15° C.-25° C.), with a relative humidity (RH) of 60%, and protected from light.

Preferably, the lawsone content of an extract A does not decrease by more than 50%, advantageously not more than 40%, particularly not more than 30%, advantageously not more than 20%, more advantageously not more than 10%, in 12 months at room temperature (15° C.-25° C.), with a relative humidity (RH) of 60%, and protected from light. Advantageously, the lawsone content of an extract A does not decrease by more than 50%, advantageously not more than 40%, particularly not more than 30%, advantageously not more than 20%, more advantageously not more than 10%, in 3 months at a temperature of 40° C. (±2) and an RH of 75% (±5).

In particular, the lawsone content of an extract A does not decrease by more than 50%, advantageously not more than 40%, particularly not more than 30%, advantageously not more than 20%, more advantageously not more than 10%, in 6 months at a temperature of 40° C. (±2) and an RH of 75% (±5).

Thus, unlike many commercially available henna extracts which have a poor lawsone content, which decreases rapidly over time, in particular by condensation with various compounds comprising an amino group, such as proteins, peptides or amino acids, the extract A as disclosed herein comprises a high and stable amount of lawsone.

The lawsone in extract A typically results from enzymatic hydrolysis of glycosylated lawsone derivatives, such as hennosides. A process for preparing such an extract is described herein below.

The extract A may further comprise luteolin, apigenin and 2,3,4,6-tetrahydroxyacetophenone.

In some embodiments, an extract A of the aerial parts of *Lawsonia inermis* containing from 7 to 60% by weight of lawsone relative to the total weight of the dry extract, wherein the lawsone results from enzymatic hydrolysis of glycosylated lawsone derivatives, such as hennosides and wherein said extract may further comprise luteolin, apigenin and 2,3,4,6-tetrahydroxyacetophenone may be prepared according to a process as described herein below.

The extract A may be further characterized by one or more of the following advantageous characteristics, advantageously by all of them:

the extract A contains from 7% to 50%, or from 10% to 50%, in particular from 15% to 40% by weight of lawsone relative to the total weight of the dry extract. Advantageously, the extract A contains at least 7%, advantageously at least 10%, at least 15%, preferably at least 20%, more advantageously at least 25% by weight of lawsone relative to the total weight of the dry extract; the percentages being expressed relative to the total weight of said dry extract (before any eventual addition of a drying carrier). The lawsone content can be determined according to the HPLC assay method described after the examples (Method 1).

the extract A does not contain more than 2%, preferably not more than 1.5%, notably not more than 1% by weight of proteins, peptides or amino acids relative to the total weight of the dry extract, advantageously from 0 to 1% by weight or from 0.1 to 1% by weight of proteins, peptides or amino acids relative to the total weight of the dry extract. The free amino acids, peptides and proteins can be assayed by ninhydrin spectrophotometry, according to the method described after the examples (Method 2).

the extract A comprises chlorophylls, in particular chlorophyll a and/or chlorophyll b, the total chlorophyll content being less than 25% by weight relative to the total weight of the dry extract, or less than 20% by weight, advantageously less than 10% by weight relative to the weight of the dry extract. In some embodiments, the extract A does not contain more than 5%, preferably not more than 2% by weight of chlorophylls relative to the total weight of the dry extract. In some embodiments, the extract A does not contain chlorophyll. The chlorophylls can be assayed by weight assay according to the method described after the examples (Method 3).

the extract A contains from 1% to 40%, advantageously from 2% to 30%, by weight of phenol compounds relative to the total weight of the dry extract. The phenol compounds content can be determined by spectrophotometry in accordance with the method described herein after the examples (method 4).

the extract A does not contain more than 5% by weight of saccharides relative to the total weight of the dry extract, advantageously from 0.1 to 5%, more advantageously from 0.5 to 5%, by weight of saccharides relative to the total weight of the dry extract. The saccharides content can be determined by colorimetric assay with dinitrosalicylic (method 5).

the extract A further contains phenol compounds, such as gallic acid, coumaric acid (in particular para-coumaric acid), 2,3,4,6-tetrahydroxyacetophenone and 3,4,5-trihydroxyacetophenone; flavonoids, such as luteolin, apigenin, catechin, 3',4',5,7-tetrahydroxyflavanone, 3',5,7-trihydroxy-4'-methylflavone; sterols, such as β-sitosterol, triterpenes, such as lupeol; and/or heterosides thereof, such as lalioside, myrciaphenone A, 1,2-dihydroxy-4-O-glycosyloxynaphtalene (also called 4-O-β-D-glucopyranoside), luteolin-4'-O-glucoside, apigenin-7-O-β-glucoside, luteolin-3'-O-glucoside, apigenin-4'-O-β-glucoside and luteolin-6-C-neohesperidoside. In some embodiments, the extract A contains phenol compounds, such as gallic acid, coumaric acid (in particular para-coumaric acid), 2,3,4,6-tetrahydroxyacetophenone and 3,4,5-trihydroxyacetophenone; flavonoids, such as luteolin, apigenin, catechin, 3',4',5,7-tetrahydroxyflavanone, 3',5,7-trihydroxy-4'-methylflavone; and/or heterosides thereof, such as lalioside, myrciaphenone A, 1,2-dihydroxy-4-O-glycosyloxynaphtalene, luteolin-4'-O-glucoside, apigenin-7-O-β-glucoside, luteolin-3'-O-glucoside, apigenin-4'-O-β-glucoside and luteolin-6-C-neohesperidoside.

the extract further contains 2,3,4,6-tetrahydroxyacetophenone, and optionally 3,4,5-trihydroxyacetophenone and/or 1,2-dihydroxy-4-O-glycosyloxynaphtalene.

the extract A further contains coumaric acid, in particular para-coumaric acid;

the extract A further contains 3,4,5-trihydroxyacetophenone and/or 1,2-dihydroxy-4-O-glycosyloxynaphtalene:

the extract further contains glycosylated luteolin, in particular luteolin-6-C-neohesperidoside.

Flavonoids, such as luteolin and apigenin have many interesting biological properties, such as free radical scavenging and antioxidative effects [Romanov et al., *Neoplasma* 2001, 48(2), 104-107] as well as anti-inflammatory activity, which, combined with their capacity to absorb UV light, are responsible for their ability to provide protection from UV radiation [Saewan et al., *JAPS* 2013, 3(9), 129-141]. Although the hair photoprotection is a topic that is not commonly addressed, the chemical effects of UV radiation and their impact on the hair shaft should not be neglected [Draelos, *Dermatol. Clin.* 2006, 24, 81-84]. Therefore, the presence of compounds that have a photoprotective effect in a cosmetic composition intended for hair dyeing is of particular interest.

Luteolin and apigenin are also well-known natural dyes, that can be used for coloring hair and textiles.

Besides, it has been shown that apigenin is a hair-growth-promoting agent [Huh et al. *Arch. Dermatol. Res.*, 2009, 301, 381-385].

Polyphenols, such as 2,3,4,6-tetrahydroxyacetophenone, and phenolic acids, such as para-coumaric acid, also have antioxidant and photoprotective properties [Nichols et al., *Arch. Dermatol. Res.* 2010, 302, 71-83]. The extract A may also contain any compound naturally present in the aerial parts of *Lawsonia inermis*, in particular in the leaves and/or branches of *Lawsonia inermis*.

In some embodiments, the extract A as disclosed herein may be in the form of a dry extract, advantageously in powder form, notably with a particle size less than 250 µm.

In some embodiments, the extract A as disclosed herein may be in the form of a standardized extract AN, in particular a standardized dry extract AN. The standardized extract AN, in particular a standardized dry extract AN, comprises the extract A of the aerial parts of *Lawsonia inermis* and a carrier.

Thus, in some embodiments, particularly advantageous when the dye composition is a cosmetic composition, the composition comprises a standardized extract AN, in particular a standardized dry extract AN, obtained by adding an inert carrier to the extract A as disclosed herein in order to standardize the lawsone content of the extract. In other words, the dye composition of the present invention comprises an extract A as disclosed herein and an inert carrier, the extract A and the carrier forming a standardized extract AN, in particular a standardized dry extract AN.

The standardized extract AN is characterized by one or the other of the following advantageous features, advantageously by all of them (percentages are expressed by weight relative to the total weight of the standardized dry extract):

the standardized extract AN comprises from 0.6% to 1.4%, advantageously from 1 to 1.3%, in particular about 1.3% by weight of lawsone;

the inert carrier is free from proteins;

the inert carrier is cosmetically-acceptable;

the carrier is selected from the group consisting of propanediol, pentanediol, glycerin, propylene glycol, methyl THF and amylic alcohol; or the carrier is selected from the group consisting of sugars or polysaccharide derivatives, such as fructose, glucose, saccharose, maltodextrins, cellulose derivatives, starch (e.g. maize, wheat or rice starch), agar-agar, gums, mucilages and polyols such as mannitol, sorbitol, xylitol, etc.

the standardized extract AN contains luteolin, apigenin and 2,3,4,6-tetrahydroxyacetophenone;

the standardized extract AN contains 3,4,5-trihydroxyacetophenone and/or 1,2-dihydroxy-4-O-glycosyloxynaphtalene;

the standardized extract AN contains coumaric acid, in particular para-coumaric acid;

the standardized extract AN contains the previously listed compounds for extract A;

the standardized dry extract AN contains from 0.2 to 3.0% by weight of phenol compounds;

the standardized dry extract AN contains glycosylated luteolin, in particular luteolin-6-C-neohesperidoside;

the standardized dry extract AN contains from 0.05 to 1.0% by weight of luteolin;

the standardized dry extract AN contains from 0.01 to 0.5% by weight of apigenin;

the standardized dry extract AN contains from 0.01 to 0.1% by weight of coumaric acid, in particular para-coumaric acid;

the standardized dry extract AN contains from 0.05 to 1.0% by weight of 2,3,4,6-tetrahydroxyacetophenone;

the standardized dry extract does not contain more than 0.2% by weight of proteins, peptides or amino acids, advantageously from 0 to 0.2% by weight, advantageously from 0.1 to 0.2% by weight, of proteins, peptides or amino acids;

the standardized dry extract AN does not contain chlorophylls;

the standardized dry extract AN does not comprise more than 0.5% by weight of saccharide compounds, advantageously from 0.01 to 0.5%, advantageously from 0.05 to 0.5% by weight of saccharide compounds;

the standardized dry extract AN complies with the stability specifications, including under accelerated conditions, previously defined for henna extract A;

the standardized dry extract AN contains at least 80%, advantageously at least 90%, notably at least 92%, in particular at least 95% by weight of carrier.

In some embodiments, the standardized dry extract AN of *Lawsonia inermis* contains from 0.6 to 1.4% by weight of lawsone relative to the total weight of the dry extract and further comprises luteolin, apigenin and 2,3,4,6-tetrahydroxyacetophenone.

In some embodiments, the standardized dry extract AN of *Lawsonia inermis* comprises, relative to the total weight of the dry extract:

from 0.05 to 1.0% by weight of luteolin;

from 0.01 to 0.5% by weight of apigenin;

from 0.01 to 1% by weight, or from 0.05 to 1.0% by weight of 2,3,4,6-tetrahydroxyacetophenone.

Preferably, the standardized extract AN is in the form of a dry extract, advantageously in powder form, notably with a particle size less than 250 µm.

Preparation of Extract A

The quantity of lawsone found in the free state in *Lawsonia inermis* leaves being actually very small, preparation of *Lawsonia inermis* extracts having high lawsone content may be cumbersome.

In the plant, the lawsone is predominantly present in the form of heterosides [Gallo et al. *Rev. Bras. Pharmacogn.* 2014, 23, 133-140; COLIPA no. C169, 2013].

Hennosides A, B and C, which are monoglycosylated lawsone derivatives, have notably been identified.

Hydrolysis of these precursors, followed by autooxidation of the resulting aglycone, leads to the formation of lawsone according to the reaction scheme indicated below.

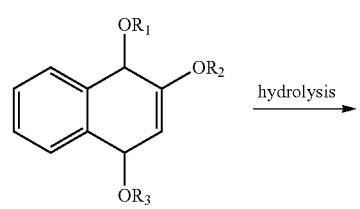

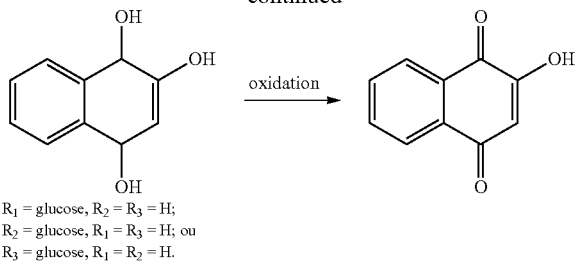

R₁ = glucose, R₂ = R₃ = H;
R₂ = glucose, R₁ = R₃ = H; ou
R₃ = glucose, R₁ = R₂ = H.

Thus, a number of known extraction processes for *Lawsonia inermis* include a step in acidic medium, typically at a pH comprised between 1 and 3, during which the hennosides are hydrolyzed.

The inventors of the present invention have developed an extraction process for *Lawsonia inermis* allowing an extract with a high lawsone content to be obtained by implementing enzymatic hydrolysis of the glycosylated lawsone derivatives. Said extract is also distinguished by its stability over time.

Thus, advantageously, the extract A of aerial parts of *Lawsonia inermis* is obtained by a process comprising the following steps:

a) Macerating the aerial parts of *Lawsonia inermis* in water, at a pH ranging from 4 to 8, in order for the glycosylated lawsone derivatives, such as hennosides, initially present in the aerial parts of *Lawsonia inermis* to be partially or totally hydrolyzed enzymatically, to provide an aqueous solution containing lawsone;

b) adding an organic solvent to the solution obtained from step a), the organic solvent being chosen from C4-C12 linear or branched alcohols or solvents having a miscibility with water which is less than 10%, advantageously less than 5% by weight at 25° C., to provide an aqueous phase and an organic phase;

c) recovering the organic phase obtained from step b); and d) concentrating the organic phase recovered from step c), to provide a lawsone-rich extract A.

In particular, the aerial parts of *Lawsonia inermis* subject to maceration in step a) are leaves, branches or mixtures thereof. The leaves can be fresh or dried, preferably dried.

Step a) is preferably conducted at a temperature ranging from 20° C. to 60° C., or from 20° C. to 50° C., in particular from 25° C. to 45° C., more particularly from 30° C. to 45° C., typically at about 40° C.

It is understood that step a) is conducted at a pH permitting the enzyme or enzymes that catalyze the hydrolysis of the glycosylated lawsone derivatives to function. In particular, step a) is conducted at a pH ranging from 4 to 8, preferably from 5 to 7.5, advantageously from 5.5 to 7.5, typically at neutral pH.

The aerial parts of *Lawsonia inermis* are typically macerated for 15 minutes to 2 h, preferably for 15 minutes to 1 h, advantageously for about 30 minutes.

In some embodiments, step (a) is performed under stirring for 15 min to 2 h, preferably for 15 minutes to 1 h, advantageously for about 30 minutes.

The aerial parts of *Lawsonia inermis* are typically macerated in a volume of water whose weight is 2 to 15 times greater, advantageously 5 to 15 times greater, more advantageously 6 to 10 times greater, typically 10 times greater than the weight of the aerial parts of *Lawsonia inermis*. For instance, when the process is implemented on 100 g of aerial parts of *Lawsonia inermis*, the volume of water used in step a) may range from 200 mL to 1500 mL, or from 500 mL to 1500 mL, advantageously from 600 mL to 1000 mL, typically is 1000 mL.

In some embodiments, a pectinase-type enzyme may be added in step a).

In some embodiments, the organic solvent is directly added to the aqueous solution obtained in step a). Then, the aqueous solution comprises the plant material and the macerating water. In these embodiments, it is to be understood that the organic solvent is directly added to the aqueous solution obtained in step a), i.e. no filtration step is performed between step a) and b).

In some embodiments, the process comprises a step of filtration between step a) and step b) allowing to separate the aerial parts of *Lawsonia inermis* from the aqueous solution containing lawsone. Alternatively, in some embodiments, the process comprises a step of filtration between step c) and step d) allowing to separate the aerial parts of *Lawsonia inermis* from the organic phase recovered/collected in step c).

An organic solvent is then added to the aqueous solution obtained in step a). The aqueous solution comprises the plant material and the macerating water. It is to be understood that the organic solvent is directly added to the aqueous solution obtained in step a), i.e. no filtration step is performed between step a) and b).

Step b) may be performed batchwise or continuously.

In some particular batchwise embodiments, step b) of process comprises the following 3 substeps:

b.1) adding an organic solvent to the aqueous solution obtained in step a);

b.2) stirring the solution obtained in step b.1) for 15 minutes to 2 h, in particular for 15 minutes to 1 h, typically for about 30 minutes; and b.3) decantating the mixture obtained in b.2), until two distinct phases are obtained, i.e. an aqueous phase and an organic phase.

Thus, the succession of substeps b.1), b.2) and b.3) leads to the formation of an aqueous phase and an organic phase.

The volume of organic solvent added during step b), in particular during step b.1), is such that the volume ratio of said organic solvent added during b) to the volume of water used during step a) is comprised between 0.25 and 2, notably between 0.5 and 2, notably between 0.8 and 1.5, in particular between 1 and 1.3.

In some embodiments, the organic solvent added during step b), in particular during step b.1), of the process herein disclosed is a weakly polar solvent. It is understood that although being weakly polar, said organic solvent does solubilize lawsone. Thus, the solubility of lawsone in the organic solvent added in b), in particular in step b.1), is greater than 70%, notably greater than 80%, advantageously greater than 90% by weight at 25° C.; the percentages being expressed relative to the total weight of lawsone present in the aqueous solution containing lawsone obtained from step a).

In some embodiments, the organic solvent added during step b), in particular during step b.1), of the process disclosed herein is selected from the group consisting of $C_1$-$C_6$ alcohols, chlorinated solvents, ketones, ethers, esters and their mixtures which satisfies the following criteria:

the miscibility of water in said organic solvent is less than 10%, advantageously than 5% by weight at 25° C., the miscibility of said organic solvent in water is less than 10%, advantageously than 5% by weight at 25° C.

In particular, the organic solvent may be selected from the group consisting of n-amylic alcohol, dichloromethane, chloroform, methyl isobutyl ketone, diethyl ether, diisopropyl ether, dibutyl ether, methyl tert-butyl ether, ($C_1$-$C_6$) alkyl acetates, such as ethyl acetate, isopropyl acetate, butyl acetate, isoamyl acetate and any mixtures thereof.

In some embodiments, the organic solvent added in step b), in particular during step b.1), is a ($C_1$-$C_6$) alkyl acetate or a mixture of ($C_1$-$C_6$) alkyl acetates, preferably selected from the group consisting of ethyl acetate, isopropyl acetate, butyl acetate, isoamyl acetate and any mixtures thereof. Preferably the organic solvent is isopropyl acetate.

In some embodiments, the organic solvent added in step b), is a $C_4$-$C_{12}$ linear or branched alcohol, preferably a $C_4$-$C_8$ linear, or branched, alcohol. Advantageously, the organic solvent is biosourced.

Advantageously, the organic solvent is a $C_4$-$C_{12}$ linear or branched alcohol selected from the group consisting of n-butanol, sec-butanol, isobutanol and any mixtures thereof, more particularly n-butanol.

$C_4$-$C_{12}$ alcohols have the advantage of not degrading during recycling operations, unlike esters such as ethyl or isopropyl acetate, or certain ketones (acetone in particular). In addition, the presence of residual water in the recycling solvent does not pose any implementation problem. So, in conclusion, this type of solvent makes it easier to recycle solvents at the industrial level.

Step c) consists in the recovery of the organic phase obtained from step b).

It is possible to repeat step b) on the aqueous phase obtained in the previous iteration of said step b). The new organic phase thus obtained is then recovered (repeat of step c)) and combined with the one resulting from the preceding iteration of step b).

Thus, in a variant of the process, step d) consists in a step d') of concentrating the combination of organic phases recovered from several iterations of step b) followed by step c).

In some embodiments, the process can contain an additional step e) of drying the lawsone-rich extract obtained from step d). At the end of said step e), the lawsone-rich extract obtained is a dry extract.

Drying step e) may be conducted according to methods well known to the skilled person. In particular, the drying step may be done by pallet dryer, vacuum drying, atomization, microwaves, zeodration or lyophilization.

In some embodiments, the process may comprise, between steps c) and d), an additional step c') of adding a carrier, and step d) is followed by the above drying step e). At the end of said step e), the obtained lawsone-rich extract is a standardized dry extract.

According to some preferred embodiments, the process does not include any step of changing the pH of the aqueous solution or the aqueous phase by addition of acid or base. According to some preferred embodiments, the process further comprises a step of extracting pigments, also called decoloration step.

The pigments extracted during the decoloration step are notably chlorophylls. However, it is understood that lawsone is not part of the pigments that the decoloration step seeks to eliminate.

The pigment extraction step can notably be done with an organic solvent that does not solubilize lawsone well. Thus, the solubility of lawsone in the organic solvent step used for the decoloration step is less than 15%, notably less than 10%, advantageously less than 5% by weight at 25° C.; the percentages being expressed relative to the total weight of lawsone contained in the extract or the solution which is undergoing the decoloration step. Preferably, the lawsone is not soluble in the organic solvent used for the pigment extraction step.

Advantageously, said organic solvent is a saturated or unsaturated hydrocarbon. In particular, said saturated hydrocarbon can be chosen from among pentane, hexane, heptane, nonane, decane, cyclohexane and mixtures thereof. Said unsaturated hydrocarbon can notably be benzene.

Preferably, the extraction step for pigments like chlorophyll is done with heptane.

The pigment extraction step done with an organic solvent may consist in a liquid-liquid or liquid-solid extraction.

When it is a liquid-liquid extraction, said step is inserted between steps a) and b) of the disclosed process.

Advantageously, the liquid-liquid extraction decoloration step using an organic solvent comprises the following 4 substeps:
i) the addition of said organic solvent to the aqueous solution obtained from step a),
ii) the stirring of the solution obtained from step i), the stirring duration being comprised between 15 minutes and 2 h, in particular between 15 minutes and 1 h, typically the stirring duration is approximately 30 minutes, and
iii) the decantation of the mixture obtained from step ii), until two distinct phases are obtained, i.e., an aqueous phase and an organic phase, and
iv) the elimination of the organic phase.

Step b) of the process is then implemented in the aqueous phase resulting from step iii). When it is a liquid-solid extraction, this step follows drying step e) of the process. Liquid-solid extraction may be done according to methods well known to the skilled person.

Alternatively, the decoloration step may be done using supercritical $CO_2$, with or without the addition of co-solvent, directly in the dry extract. The chlorophyll is entrained by the supercritical $CO_2$. The residue is the decolored dry extract.

Extract B of the Aerial Parts of *Lawsonia inermis*

The dye composition of the present invention comprises a second particular Henna extract, referred herein as "extract B". Extracts A and B are combined to provide a dye composition.

This extract B is characterized by a low lawsone content.

Thus, the extract B contains less than 0.6% by weight, relative to the weight of the dry extract, of lawsone, advantageously less than 0.5% by weight, more advantageously less than 0.4% by weight, for example from 0 to 0.6%, particularly from 0.05 to 0.6%, more particularly from 0.1 to 0.5%, in particular from 0.1 to 0.4%, better still approximately about 0.2% by weight, of lawsone relative to the total weight of the dry extract.

The lawsone content can be determined by the HPLC assay method described in the following examples (Method 1).

The extract B comprises phenol compounds, such as tannins, phloroglucinol derivatives, naphthoquinone derivatives, flavonoids, and combinations thereof.

In particular, the phenol compounds may be chosen from gallic acid, coumaric acid, and/or heterosides of such compounds and combinations thereof; in particular gallic acid.

In particular, the phloroglucinol derivatives are selected from the group consisting of 2,3,4,6-tetrahydroxyacetophenone, 1,3,6,7 tetrahydroxyxanthone, phloroacetophenone, myrciaphenone A, lalioside, and/or heterosides of such derivatives such as polygoacetophenoside, and combinations thereof.

In particular, the naphthoquinone derivatives are chosen from isonaphthazarin and/or heterosides of such derivatives such as 1,2,4-trihydroxynaphthalen-1-O-glucoside, and combinations thereof.

In particular, the flavonoid derivatives are chosen from luteolin and/or heterosides of such derivatives such as luteolin-4'-O-glucoside, luteolin-7-O-glucoside, and combinations thereof.

In some embodiments, the phenol compounds of extract B include:
- tannins, in particular hydrolyzable tannins, more particularly gallic tannins;
- gallic acid;
- luteolin and heterosides thereof, in particular glycosylated derivatives thereof;
- apigenin;
- 2,3,4,6-tetrahydroxyacetophenone;
- 1,3,6,7-tetrahydroxyxanthone.

In some embodiments, the phenol compounds of extract B are selected from the group consisting of:
- gallic acid, coumaric acid, and/or heterosides of such compounds and combinations thereof;
- tannins, in particular gallic tannins;
- phloroglucinol derivatives, such as 2,3,4,6-tetrahydroxyacetophenone and
- flavonoid derivatives, such as luteolin, apigenin and/or heterosides of such derivatives and combinations thereof.

In some embodiments, extract B is characterized by a luteolin content of from 0.05 to 0.5%, particularly from 0.1 to 0.3%, by weight relative to the total weight of the dry extract.

In some embodiments, extract B is characterized by an apigenin content of 0.01 to 0.75%, particularly from 0.05 to 0.5%, by weight relative to the total weight of the dry extract.

In some embodiments, extract B is characterized by a 2,3,4,6-tetrahydroxyacetophenone content of from 0.01 to 0.5%, particularly from 0.02 to 0.1%, by weight relative to the total weight of the dry extract.

In some embodiments, extract B is characterized by a gallic acid content of from 0.05 to 0.5%, particularly from 0.1 to 0.3%, by weight relative to the total weight of the dry extract. The quantity of phenol compounds contained in the extract B is of at least 10%, particularly at least 15% by weight, relative to the total weight of the dry extract. In particular, the extract B comprises from 10 to 35%, advantageously from 15 to 35%, more advantageously from 15 to 30% by weight of phenol compounds relative to the total weight of the dry extract.

The content in phenol compounds are expressed by reference to the content of pyrogallol (Method 4).

The extract B comprises a large quantity of compounds of the saccharide type, at least 60% by weight, advantageously at least 65% by weight, more advantageously at least 70% by weight, for example from 60 to 80% by weight, particularly from 70 to 75% by weight of saccharide compounds, including polysaccharides, relative to the total weight of the dry extract.

The saccharide compounds may further comprise monosaccharaides, disaccharides and combinations thereof. In particular, the polysaccharides are predominant by weight, i.e. they typically constitute more than 50% by weight, advantageously more than 60% by weight, more advantageously more than 70% by weight, even more advantageously more than 80% by weight, even more advantageously more than 90% by weight, of all the saccharides present in the extract.

In particular, extract B may comprise mucilages as polysaccharides.

Mucilages are plant substances, made up of polysaccharides or proteosaccharides, which swell on contact with water and take on a viscous consistency, sometimes tacky, similar to gelatin.

Mucilages are compounds of large, more or less branched polymeric structures constructed from several different saccharide units or uronic acid units (uronic acids are carboxylic acids derived from sugars). They are very hydrophilic and are able to trap water (and other molecules) in their cage-like structures to form a gel.

The saccharide compound content can be determined by dinitrosalicylic colorimetric assay (Method 5).

The extract B may further comprise organic acid(s). The content of organic acid(s) may be of at least 2% by weight, advantageously at least 3% by weight, more advantageously at least 4% by weight, for example from 2 to 8% by weight of organic acid(s), particularly from 4 to 8% by weight, relative to the total weight of the dry extract.

The organic acids of extract B notably comprise hydroxy-acids, i.e., hydrocarbon compounds bearing at least one carboxylic acid —COOH function and at least one alcohol —OH function, advantageously the at least one alcohol function is in the alpha position of a carboxylic acid function (i.e., borne by a carbon atom adjacent to the carbon atom bearing the carboxylic acid function). The organic acids, in particular carboxylic, of extract B are advantageously carboxylic acids whose linear, branch or ring-containing alkyl chain comprises 4 to 8 carbon atoms, advantageously 4 to 6 carbon atoms. The carboxylic acids are, in particular, selected in the group consisting of succinic acid, ascorbic acid, malic acid, and combinations thereof. The organic acids, such as malic acid, succinic acid and ascorbic acid, may be assayed by known enzymatic or spectrophotometric methods available to the skilled person, notably by HPLC (Method 6).

These organic acids contribute to promoting the attachment of lawsone to the keratin fiber. These organic acids also contribute to conferring a particular shine to the hair thus colored and hydration of the fiber.

Lactones can also be found in the extract B, in a quantity generally less than 10% by weight, relative to the total weight of the dry extract.

The extract B may contain protein compounds such as peptides, amino acids and protein in a quantity ranging from 5 to 10% by weight relative to the weight of the dry extract.

The extract B may be further characterized by one or more of the following advantageous characteristics, advantageously by all of them (percentages are expressed in weight relative to the total weight of the dry extract B):
- Extract B comprises less than 0.6% by weight of lawsone, advantageously less than 0.5%, more advantageously less than 0.4%, for example from 0 to 0.6%;
- Extract B comprises at least 15% by weight of phenol compounds, notably tannins;
- Extract B comprises gallic acid, advantageously in a content ranging from 0.1 to 0.3% by weight;
- Extract B comprises 2,3,4,6-tetrahydroxyacetophenone, advantageously in a content ranging from 0.02 to 0.1% by weight;
- Extract B comprises luteolin, advantageously in a content ranging from 0.1 to 0.3% by weight;

Extract B comprises apigenin, advantageously in a content ranging from 0.05 to 0.5% by weight;

Extract B comprises 1,3,6,7-tetrahydroxyxanthone;

Extract B comprises from 60 to 80% of saccharide compounds, predominantly polysaccharides, by weight, including mucilages;

Extract B contains 2 to 8% by weight of organic acids, including malic acid, succinic acid and ascorbic acid.

In some embodiments, the extract B can be in the dry form, advantageously in the powder forum, notably of particle size less than 250 μm.

It was observed that this extract B, combined with extract A allows:

broadening the range of colors, and in particular to access the color chart sought in hair coloring;

improving the attachment of the extract A onto fibers, in particular keratin fibers;

adding shine to keratin fibers, especially hair.

Process for Obtaining Extract B

The Applicant has developed a process for obtaining extract B from *Lawsonia inermis* making it possible to obtain an extract with a low lawsone content, therefore having a weak dyeing effect, but rich in compounds that make it possible to obtain dyeing effects and benefits for keratin fibers, such as phenolic compounds and saccharide compounds as explained below.

The present invention reflects a desire to set up synthesis pathways that are greener and that make it possible to claim that the active ingredients thus obtained are natural.

Thus, advantageously, extract B of aerial parts of *Lawsonia inermis* is an extract obtained by an aqueous, hydroalcoholic or alcoholic extraction.

Henna extract B can be obtained by aqueous extraction from crushed leaves at room temperature or higher temperature, which temperatures can range from 20° C. to 180° C. and at atmospheric or supercritical pressure. After liquid/liquid separation, the filtrate is sterilized by standard sterilization methods (pasteurization, flash pasteurization, etc.) then dry concentrated by standard drying methods known to the person skilled in the art (vacuum drying, lyophilization, microwave, etc.).

Advantageously, an alcohol miscible with water, in particular ethanol or ter-butanol, preferably ethanol, can be added before liquid/liquid separation to facilitate the filtration and solubilization of weakly polar compounds.

The extraction can be carried out by different technologies, in particular so-called "green" technologies, such as at atmospheric pressure (possibly using means to assist the extraction such as ultrasound, microwaves, leaching, maceration, decoction, etc.) or at high pressures, in particular with water in the subcritical state with or without cosolvent such as ethanol at temperatures of between 20° C. and 250° C.

In some embodiments, the extract B of aerial parts of *Lawsonia inermis* is an extract obtained by a method comprising the following steps:

a) Mixing aerial parts, particularly crushed leaves, of *Lawsonia inermis* in water particularly with a plant/water w/v ratio comprised between 1/2 and 1/10, advantageously between 1/4 and 1/8;

b) Stirring the mixture obtained at a temperature ranging from 30° C. to 50° C.; c) Optionally adding alcohol, such as ethanol;

d) Stirring and recovering the liquid phase;

e) Concentrating the liquid phase obtained in step d) to obtain an extract B.

In particular, the aerial parts of *Lawsonia inermis* subjected to maceration in step a) are leaves, which can be fresh or dried, preferably dried, branches or a mixture of the two, preferably finely crushed.

In one particular embodiment, a pectinase-type enzyme can be added in step a).

Advantageously, stirring can be obtained by all the methods well known to the skilled person.

Likewise, the aqueous or hydroalcoholic liquid phase can be recovered by any liquid-solid separation technique known to the skilled person, such as filtration, centrifugation or decantation, for example.

The duration of stirring is advantageously comprised between 15 minutes and 2 h, in particular between 15 minutes and 1 h, advantageously it is approximately 30 minutes.

The volume of alcohol, added during step b), when this is the case, is such that the mixture obtained comprises from 30 to 90% v/v of alcohol, advantageously 50 to 80% v/v of alcohol. In addition to facilitating the extraction of hydrophilic compounds, alcohol, such as ethanol, also disinfects and decontaminates the mixture.

Also, alternatively, the optional step c) of adding the alcohol, such as ethanol, can be replaced by a decontamination and/or sterilization step by an alternative and equivalent technique known to the person skilled in the art, such as by heating, for example using steam injection, or microwave treatment or any other suitable decontaminating treatment. In one embodiment, the method can contain an additional step f) of drying the extract obtained from step e). At the end of said step f), extract B obtained is a dry extract. Drying step f) can be done according to methods well-known to the skilled person. In particular, the drying step may be done by paddle dryer, vacuum drying, atomization, microwave, zeodration or lyophilization.

Alternatively extract B can be obtained according to the following process:

a) macerating the aerial parts of *Lawsonia inermis* in water, performed at a pH ranging from 4 to 8, in order for the glycosylated derivatives of lawsone, such as hennosides, initially present in the aerial parts of *Lawsonia inermis* to be partially or completely hydrolyzed enzymatically, resulting in the production of an aqueous solution containing lawsone;

b) adding an organic solvent to the aqueous solution obtained at the end of step a), the organic solvent being chosen from $C_4$-$C_{12}$ linear, or branched, alcohols or solvents for which the miscibility of water is less than 10%, advantageously 5% by weight at 25° C., resulting in the formation of an aqueous phase and an organic phase;

c') recovering the aqueous phase obtained at the end of step b); and d') concentrating the aqueous phase recovered at the end of step c'), to obtain an extract B low in lawsone.

Thus, extract B may be obtained by a method implementing steps a) and b) of the method previously described for obtaining extract A. However, subsequently, the recovered phase is the aqueous phase.

Advantageously, steps a) and b) are such as described previously for the method for obtaining extract 1.

Step c') consists in the recovery of the aqueous phase and its concentration in order to obtain the extract B.

The method may also comprise, between steps c') and d'), a decontamination and/or sterilization step by any technique known to the person skilled in the art such as by heating, for example using steam injection, or microwave treatment or any other suitable decontaminating treatment.

In one embodiment, the method can contain an additional step e) of drying the extract low in lawsone obtained from step d'). At the end of said step e'), the extract low in lawsone obtained is a dry extract. Drying step e) can be done according to methods well known to the skilled person. In particular, the drying step may be done by paddle dryer, vacuum drying, atomization, microwave, zeodration or lyophilization.

Mixture of Henna Extracts A and B

Henna extracts A and B as disclosed herein above are mixed to provide the dye composition of the present invention. Surprisingly, the ratio by weight of one to the other will have an effect on the dye obtained and therefore, by varying this ratio, it is possible to access a broad color spectrum. The composition of the two henna extracts A and B permits obtaining a palette of shades both in colors and in reflects (tone).

In some embodiments of the method of the invention, extract A is mixed with extract B according to a B/A weight ratio greater than or equal to 1. According to one particular embodiment, the B/A weight ratio may be comprised between 1 and 10/1. Here, we mean the ratio of the dry extracts, the extract A being a standardized dry extract.

According to an alternative method, the extract A can be mixed with the extract B according to a B/A weight ratio less than 1, advantageously ranging from 1/10 to 1. Here, we mean the ratio of the dry extract, the extract A being a standardized dry extract. According to a particular embodiment, the B/A weight ratio may be comprised between 1/10 and 10/1, for example between 8/1 and 1/3. Here, we mean the ratio of the dry extract, the extract A being a standardized dry extract.

Beneficial Agent

The method according to the invention can also comprise providing a beneficial agent, in particular an agent promoting the attachment of the dye to its substrate, notably cellulose fibers and/or keratin fibers. Extract A, extract B and the beneficial agent are then mixed to provide a dye composition.

The beneficial agent is preferably in the dry form, advantageously in the powder forum, notably of particle size less than 250 µm.

The beneficial agent can also be a plant extract or plant powder.

For example, cassia (neutral henna), can be used to promote the attachment to cellulose and/or keratin fibers of henna extract A. It can also provide shine to the hair.

For example, aloe vera, in particular the juice extract of aloe vera leaves, can be used as a natural mordant, i.e., as a compound that promotes the adhesion of the dyeing agent. It can also nourish and hydrate keratin fibers and protect them from UV radiation.

Aloe vera also comprises anthraquinones, such as aloin and aloe emodin, resins, tannins and polysaccharides. A juice/gel can be extracted from aloe vera leaves that mainly comprises water and polysaccharides, such as pectins, hemicelluloses, glucomannans, acemannans and mannose derivatives. This juice/gel can also comprise amino acids, lipids, sterols such as lupeol and campesterol, and enzymes.

The beneficial agent can be a fructan, such as inulin for its properties of coating the keratin fiber.

Composition

The composition obtained according to the method of the invention comprises the henna extract A and the henna extract B. It may further comprise a beneficial agent as disclosed herein above and/or one or more further dyeing agents as disclosed herein below.

Advantageously, it may also comprise the addition of a limited number of dyeing agents not exceeding 5 additional dyeing agents, advantageously not more than 3 additional dyeing agents, more advantageously not more than 2 additional dyeing agents, even more advantageously not more than 1 additional dyeing agent. In one advantageous embodiment, the composition comprises only the henna extracts A and B as the dyeing agents.

It is particularly advantageous to note that by means of the combination of two extracts derived from the same plant, i.e. henna, a broad color pallet can be obtained, in particular the entire color pallet sought in hair dyeing, both in color and reflects, thus using a limited number of dyeing agents. This limited number reduces the risks of intolerance and incompatibilities and is more economical.

Moreover, the combination according to the invention provides a dye composition:
  that is natural, free of animal products, i.e., based on dye
    active ingredients derived from plants, microorganisms
    or microalgae;
  with a short exposure time, advantageously less than an
    hour for dyeing hair;
  preferably in a single application, including for dyeing
    hair;
  preferably organic and vegan;
  permitting good color retention, including after several
    washes, including after 10 shampoos, advantageously
    15 shampoos, for a hair dye.

A hair dye that avoids the use of hydrogen peroxide and alkaline chemical agents is also sought.

Particularly advantageous combinations are:
  henna extract A, in particular henna extract AN, and a
    henna extract B
  henna extract A, in particular henna extract AN, a henna
    extract B and a logwood powder
  henna extract A, in particular henna extract AN, a henna
    extract B, and a sorghum extract
  henna extract A, in particular henna extract AN, a henna
    extract B, and a sorghum powder
  henna extract A, in particular henna extract AN, a henna
    extract B, and a gardenia extract
  henna extract A, in particular henna extract AN, a henna
    extract B, and a gardenia powder
  henna extract A, in particular henna extract AN, a henna
    extract B, and chlorophyllin
  henna extract A, in particular henna extract AN, a henna
    extract B, and an *Indigofera* plant extract
  henna extract A, in particular henna extract AN, a henna
    extract B, and an *Indigofera* plant powder.

In one particular embodiment, the dye composition obtained according to the method of the invention comprises from 10 to 90%, notably from 10 to 50%, or from 50 to 90% by weight of the standardized henna extract AN, the weight of the standardized extract being expressed in dry extract, relative to the total dry weight of the composition.

In one particular embodiment, the dye composition obtained according to the method of the invention comprises from 10 to 90%, notably from 10 to 50%, or from 50 to 90% by weight of the henna extract B, the weight of the extract B being expressed in dry extract, relative to the total dry weight of the composition.

The extracts, and in particular henna extract A, may be standardized, the carrier will be found in the composition.

The carrier may notably be selected from propanediol, pentanediol, glycerine, propylene glycol, methyl THF and amylic alcohol.

When the dye composition according to the invention is in powder form, the carrier is preferably selected from sugars and polysaccharide derivatives, such as fructose, glucose, saccharose, maltodextrins, cellulose derivatives, starch (e.g. maize, wheat or rice starch), agar-agar, gums, mucilages, and polyols such as mannitol, sorbitol, xylitol, etc. In particular, the carrier is selected from fructose, maltodextrins and starch, in particular rice starch.

When the dye composition according to the invention is in the powder form, the skilled person may adjust its particle size by any method well known to them.

In particular, a dye composition according to the invention may be in the powder form, of particle size less than 250 μm.

The composition may further comprise one or more acceptable excipients, in particular one or more cosmetically-acceptable excipients suitable for application on human keratin fibers (such as disclosed herein below).

Advantageously, the composition is free of the stabilizers usually present in henna compositions to stabilize lawsone.

Advantageously, the dye composition according to the invention is free of additives consisting of synthetic dyes, such as diaminotoluenes and diaminobenzenes, in particular PPD (para-phenylenediamine) which is the most commonly used, or heavy metals [Wang et al. *J. environ. Anal. Toxicol.* 2016, 6(3); Wang et al. *J. Chromatogr. B* 2011, 879, 1795-1801].

The dye composition according to the invention may also be a printing ink comprising extract A, extract B and suitable excipients, in particular selected from oils and resins, as well as mixtures thereof.

Another Dyeing Agent C

The composition according to the invention may further comprise a dyeing agent C derived from a tinctorial plant other than *Lawsonia inermis*, or from microorganisms or microalgae. Thus, the method of the present invention may further comprise the step of providing a dyeing agent C as disclosed herein.

Preferably, the dyeing agent C is in the dry form, advantageously in the powder forum, notably of particle size less than 250 μm.

The dyeing agent C may be a powder of a tinctorial plant, other than *Lawsonia inermis*, or of microorganisms or microalgae. The dyeing agent C may also be an extract of a tinctorial plant, other than *Lawsonia inermis*, or of microorganisms or microalgae. The extract will most often be an aqueous extract or a hydroalcoholic or alcoholic extract.

Advantageously, the dyeing agent C comes from at least one tinctorial plant, other than *Lawsonia inermis*, selected from *Indigofera* plants, source plants of red pigment, source plants of red or purple to black pigment, source plants of yellow pigment, source plants of red to blue green pigment, source plants of tannins, source plants of chestnut pigment and combinations thereof.

In particular, the *Indigofera* plants are selected from the true indigo tree (*Indigofera tinctoria*), dyer's knotweed (*Polygonum tinctorium* or *Persicaria tinctoria*), dyer's woad (*Isatis tinctoria* L.), *Couroupita guianensis* (Cannon ball tree), wild indigo (*Baptisia tinctoria*), dyer's croton (*Chrozophora tinctoria*), dyer's oleander (*Wrightia tinctoria*), Yoruba indigo (*Philenoptera cyanescens*=*Lonchocarpus cyanescens*), *L. laxiflorus* (*Lonchocarpus laxiflorus*), *Marsdenia tinctoria* (Asclepiadaceae), Chinese rain bell (*Strobilanthes cusia* or *Strobilanthes flaccidifolius*) and combinations thereof.

Advantageously, the dyeing agent C comprises indirubin and/or leucoindigo.

Advantageously, the dyeing agent C is an extract of indigo leaves, in particular an aqueous or hydroalcoholic or alcoholic extract, or a powder of indigo leaves.

Advantageously, the dyeing agent C is an extract of dyer's knotweed leaves, in particular an aqueous or hydroalcoholic or alcoholic extract, or a powder of dyer's knotweed leaves.

Advantageously, the dyeing agent C is an extract of dyer's woad leaves, in particular an aqueous or hydroalcoholic or alcoholic extract, or a powder of dyer's woad leaves.

Advantageously, the dyeing agent C is an extract of *Couroupita guianensis* flowers and/or fruits, in particular an aqueous or hydroalcoholic or alcoholic extract, or a powder of *Couroupita guianensis* flowers and/or fruits.

Advantageously, the dyeing agent C is an extract of the whole wild indigo plant, in particular an aqueous or hydroalcoholic or alcoholic extract, or a powder of the whole wild indigo plant.

Advantageously, the dyeing agent C is an extract of the whole dyer's croton plant, in particular an aqueous or hydroalcoholic or alcoholic extract, or a powder of the whole dyer's croton plant.

Advantageously, the dyeing agent C is an extract of the whole dyer's oleander plant, in particular an aqueous or hydroalcoholic or alcoholic extract, or a powder of the whole dyer's oleander plant.

Advantageously, the dyeing agent C is an extract of Yoruba indigo leaves, in particular an aqueous or hydroalcoholic or alcoholic extract, or a powder of Yoruba indigo leaves.

Advantageously, the dyeing agent C is an extract of *L. laxiflorus* leaves, in particular an aqueous or hydroalcoholic or alcoholic extract, or a powder of *L. laxiflorus* leaves.

Advantageously, the dyeing agent C is an extract of the whole *Marsdenia tinctoria* plant, in particular an aqueous or hydroalcoholic or alcoholic extract, or a powder of the whole *Marsdenia tinctoria* plant.

Advantageously, the dyeing agent C is an extract of the whole Chinese rain bell plant, in particular an aqueous or hydroalcoholic or alcoholic extract, or a powder of the whole Chinese rain bell plant.

Advantageously, the dyeing agent C is derived from at least one tinctorial plant that is a source of red pigment. In particular, source plants of red pigment are selected from among sorghum, hibiscus and combinations thereof.

Advantageously, the dyeing agent C comprises anthocyanins.

Advantageously, the dyeing agent C is an aqueous extract or hydroalcoholic extract of aerial parts, in particular the stem, of sorghum or a powder of aerial parts, in particular the stem, of sorghum. In the case of an extract, the extraction solvent, advantageously aqueous or hydroalcoholic, is advantageously at an acidic pH, advantageously below 6. In the case of a hydroalcoholic extract, the alcohol is advantageously miscible with water, such as ethanol.

Advantageously, the dyeing agent C is an aqueous extract or hydroalcoholic extract of hibiscus flowers, in particular dried flowers (karkade), or a powder of hibiscus flowers, in particular dried flowers (karkade). In the case of an extract, the extraction solvent, advantageously aqueous or hydroalcoholic, is advantageously at an acidic pH, advantageously below 6. In the case of a hydroalcoholic extract, the alcohol is advantageously miscible with water, such as ethanol.

Advantageously, the dyeing agent C is derived from at least one tinctorial plant that is a source of red or violet to black pigment. In particular, the plant source of red or violet to black pigment is logwood.

Advantageously, the dyeing agent C is an aqueous extract or hydroalcoholic extract of logwood wood, in particular heartwood, or a powder of logwood wood, in particular heartwood. In the case of a hydroalcoholic extract, the alcohol is advantageously miscible with water, such as ethanol.

Advantageously, the dyeing agent C is derived from at least one tinctorial plant that is a source of yellow pigment. In particular, the yellow pigment source plants are selected from gardenia, turmeric, saffron, birch, chamomile, reseda and combinations thereof.

Advantageously, the dyeing agent C comprises crocins.

Advantageously, the dyeing agent C is an aqueous extract or hydroalcoholic extract of gardenia fruit or a power of gardenia fruit. Such a dyeing agent C can be extracted from the gardenia described in application WO2018162760. In particular, the gardenia extract or powder contains a fraction by weight of crocins comprised between 0.1 and 10%, preferably between 1 and 5%, relative to the total weight of the dry extract or the dry powder. The gardenia extract can be a fluid, aqueous or hydroalcoholic extract, or a dry extract. In particular, it is an aqueous extract. A fluid gardenia extract, more particularly an aqueous or hydroalcoholic gardenia extract, can be in the form of the liquid fraction (more or less viscous) obtained after extraction and liquid-solid separation and containing from 20% to 60% of dry extract, more particularly 30 to 50% of dry extract and more particularly still, approximately 40% of dry extract in the aqueous or hydroalcoholic solvent. The extract can also be in the form of a dry extract once the aqueous or hydroalcoholic solvent evaporates from the fluid extract. This extract is typically pulverulent and has a mean particle size comprised between 0.1 µm and 250 µm, particularly between 1 µm and 250 µm. Advantageously, the dyeing agent C is an aqueous extract or hydroalcoholic extract of turmeric rhizome or a powder of turmeric rhizome. In the case of a hydroalcoholic extract, the alcohol is advantageously miscible with water, such as ethanol.

Advantageously, the dyeing agent C is an aqueous extract or hydroalcoholic extract of saffron stigma or a powder of saffron stigma. In the case of a hydroalcoholic extract, the alcohol is advantageously miscible with water, such as ethanol.

Advantageously, the dyeing agent C is an aqueous extract or hydroalcoholic extract of birch leaves or a powder of birch leaves. In the case of a hydroalcoholic extract, the alcohol is advantageously miscible with water, such as ethanol.

Advantageously, the dyeing agent C is an aqueous extract or hydroalcoholic extract of chamomile flowers, especially the ligule, or a powder of chamomile flowers, especially the ligule. In the case of a hydroalcoholic extract, the alcohol is advantageously miscible with water, such as ethanol.

Advantageously, the dyeing agent C is an aqueous extract or hydroalcoholic extract of reseda roots or a powder of reseda roots. In the case of a hydroalcoholic extract, the alcohol is advantageously miscible with water, such as ethanol.

Advantageously, the dyeing agent C is derived from at least one tinctorial plant that is a source of green-blue pigment. In particular, source plants of green-blue pigment are selected from among elderberry, blueberry, chokeberry and combinations thereof.

Advantageously, the dyeing agent C is an aqueous extract or hydroalcoholic extract of elderberry fruit or a powder of elderberry fruit. In the case of a hydroalcoholic extract, the alcohol is advantageously miscible with water, such as ethanol.

Advantageously, the dyeing agent C is an aqueous extract or hydroalcoholic extract of blueberry fruit or a powder of blueberry fruit. In the case of a hydroalcoholic extract, the alcohol is advantageously miscible with water, such as ethanol.

Advantageously, the dyeing agent C is an aqueous extract or hydroalcoholic extract of choke berry fruit or a powder of chokeberry fruit. In the case of a hydroalcoholic extract, the alcohol is advantageously miscible with water, such as ethanol.

Advantageously, the dyeing agent C is derived from at least one tinctorial plant that is a source of tannins. In particular, source plants of tannins are selected from among chestnut, *Emblica officinalis*, pomegranate and combinations thereof.

Here, tannin plants are sought to darken the color, in particular to gray or dark chestnut hues.

Advantageously, the dyeing agent C comprises tannins.

Advantageously, the dyeing agent C is an aqueous extract or hydroalcoholic extract of chestnut wood or a powder of chestnut wood. In the case of a hydroalcoholic extract, the alcohol is advantageously miscible with water, such as ethanol.

Advantageously, the dyeing agent C is an aqueous extract or hydroalcoholic extract of *Emblica officinalis* fruit or a powder of *Emblica officinalis* fruit. In the case of a hydroalcoholic extract, the alcohol is advantageously miscible with water, such as ethanol.

Advantageously, the dyeing agent C is an aqueous extract or hydroalcoholic extract of pomegranate fruits, especially the pericarp or a powder of pomegranate fruits, especially the pericarp. In the case of a hydroalcoholic extract, the alcohol is advantageously miscible with water, such as ethanol.

Advantageously, the dyeing agent C is derived from at least one tinctorial plant that is a source of chestnut pigment. In particular, the plant source of chestnut pigment is rhapontic.

Advantageously, the dyeing agent C is an aqueous extract or hydroalcoholic extract of rhapontic roots or a powder of rhapontic roots (*Rheum rhaponticum* root powder).

All the extracts and powders named above can have the "organic" label, i.e., not involving a chemical synthesis step, and can be obtained by environmentally-responsible methods. They may also be called "vegan".

The invention can also provide the use of extracts that are obtained by semisynthetic or synthetic methods.

In particular, the dyeing agent C may be chlorophyllin. Chlorophyllin is a source of green pigment.

Chlorophyllin can be obtained by extraction according to a semisynthetic method involving a chlorophyll saponification step.

Chlorophyll-rich plants can notably be selected from alfalfa, white mulberry, nettle, algae, and combinations thereof.

Chlorophyll can be extracted, for example, from aerial parts of alfalfa with an organic solvent such as acetone, alcohols, alkanes (hexane or heptane) or supercritical $CO_2$.

Chlorophyll can be extracted, for example, from aerial parts of white mulberry with an organic solvent such as acetone, alcohols, alkanes (hexane or heptane) or supercritical $CO_2$.

Chlorophyll can be extracted, for example, from aerial parts of nettle with an organic solvent such as acetone, alcohols, alkanes (hexane or heptane) or supercritical $CO_2$.

Chlorophyll can be extracted, for example, from the thallus of algae with an organic solvent such as acetone, alcohols, alkanes (hexane or heptane) or supercritical $CO_2$.

The composition may comprise at least 5% by weight of a dyeing agent C, by dry weight relative to the dry weight of the composition.

Cosmetic Composition

The composition obtained by the method of the present invention is preferably a cosmetic composition. It can be formulated to be administrated by external topical route.

The cosmetic composition can be formulated in the form of various preparations suitable for topical administration, such as creams, emulsions, milks, ointments, lotions, oils, aqueous or hydroalcoholic or glycolic solutions, powders, sprays, shampoos, varnishes or any other product for external application.

The dyeing cosmetic composition advantageously comprises at least one cosmetically-acceptable excipient.

Notably, the composition according to the present invention can also comprise at least one cosmetically-acceptable excipient known to the person skilled in the art, chosen from surfactants, texture and/or feel agents, preservatives, fragrances, dyes, chemical or mineral UV filters, hydrating agents, mineral waters, acidity corrector, etc. The person skilled in the art knows how to adapt the formulation of the composition according to the invention using their general knowledge.

In particular, the composition may comprise at least one acidity corrector, advantageously selected from organic acids, in particular citric acid, acetic acid, carbonates and bicarbonates, in particular sodium, calcium or potassium bicarbonate.

In particular, the composition may comprise at least one texture and/or feel agent, advantageously chosen from maltodextrin, fructans such as inulin, bamboo silica cellulose, polysaccharides such as guar gum, xanthan gum, alginate, carrageenan, locust bean gum, gum arabic, acacia gum, konjac, pectins, as well as combinations thereof, advantageously the composition comprises xanthan gum or the xanthan gum-acacia gum combination. The cellulose can notably be a cellulose ether, such as carboxymethylcellulose or hydroxypropyl methylcellulose.

Kits or Combination Products

The invention also relates to a kit or combination product, comprising the following components: a component (X) comprising a combination of the extracts A and B of aerial parts of *Lawsonia inermis* and a component (Y) comprising at least one cosmetically-acceptable excipient.

This excipient can be defined as previously for the cosmetic composition, and in particular be selected in the group comprising a texture and/or feel agent, an acidity corrector and mixtures thereof.

Advantageously, component (Y) is a haircare product selected in the group comprising shampoo, conditioner, hair balm, hair lotion, hair cream, etc.

Component (X) is advantageously in the dry form, notably powder.

Methods and Uses

The invention also relates to the use of a composition obtained according to a method of the invention for cosmetic dyeing of keratin fibers, notably human. In such a case, preferably the standardized henna extract AN is used.

It has been effectively seen that the composition can comprise a limited number of dyeing agents, in particular derived from a single plant, henna, but nevertheless cover the entire color range sought for a hair dye, whether tone-on-tone or permanent. The composition of the two henna extracts A and B permits obtaining a palette of shades both in colors and in reflects (tone). The dye can also more effectively cover white hair.

Another advantage of the method according to the invention, and the composition according to the invention, is that the color obtained, notably on keratin fibers such as hair, is maintained despite repeated washing.

Thus, advantageously, the colored keratin fibers do not exhibit a reduction in shine of more than 8 units, advantageously not more than 6 units, more advantageously not more than 5 units, even more advantageously not more than 4 units, even more advantageously not more than 3 units, following 10, advantageously 15, post-dye washes, shine assessed by measuring the dE* parameter, according to the protocol described in the examples.

Another advantage of the invention, and the composition according to the invention, is that dyeing is obtained with a short exposure time, advantageously less than one hour for a hair dye. It can also be obtained in a single application.

The present invention also relates to a cosmetic method for keratin fiber dyeing comprising the application of an aqueous composition comprising a composition according to the invention onto keratin fibers, optionally followed by rinsing.

In particular, the cosmetic method for dyeing keratin fibers, notably human, comprises the following steps:

a) Providing a composition according to the invention, in particular in dry form, notably in powder form b) Preparing an aqueous composition, by adding to the powder of step a) an aqueous composition, notably water, at a temperature between 20° C. and 98° C. and mixing c) Applying onto keratin fibers, optionally while heating the fibers thus treated d) Rinsing e) Optionally, repeating steps c) and d).

Advantageously, steps c) and d) are not repeated.

It is observed that a small quantity of composition according to the invention, with a small quantity of water, could suffice for dyeing the hair of an adult head. Traditionally, with a natural dye comprising a plant powder or extract, it is recommended to mix at least 100 g of powder with at least 300 g of water, which leads to a "poultice" that is very thick and not very pleasant to handle and apply.

According to the invention, during step a), advantageously less than 50 g of powder of the composition according to the invention are provided, more advantageously less than 30 g, even more advantageously less than 25 g, for example from 15 g to 30 g, advantageously from 15 g to 25 g, more advantageously approximately 20 g.

During step b) water is advantageously added in a sufficient quantity to prepare a composition of 100 g to 150 g.

The addition of water can be ambient temperature water or hot water (hot tap water). The hot water temperature can be at least 50° C., advantageously at least 70° C., or even at least 90° C., such as is easily obtained in a tea kettle.

Thus, 100 g or 150 g of aqueous composition suffice to obtain a preparation that can be applied to the head. The composition obtained has a pleasant formulation, unlike the very thick and unpleasant "poultice" aspect of known natural dyes.

The application steps can be those already used for chemical hair dye, with an exposure time step before the rinsing step. In particular, the exposure time step also comprises a heating step, in particular at a temperature comprised between 25° C. and 65° C., advantageously between 30° C. and 60° C., in particular 55° C. or in particular 35° C. Alternatively, the exposure time step can be carried out at room temperature, ranging notably from 20° C. to 30° C., without additional heat input and thus without the heating step. Advantageously, the exposure time is short, i.e., less than 1 h, preferably less than 45 minutes.

Advantageously, application step c) is carried out at a temperature comprised between 20° C. and 55° C. for a time comprised between 15 min and 1 hour, more advantageously between 15 min and 45 min.

Application step c) can be done on dry or wet keratin fiber strands.

In one embodiment, the dye is a tone-on-tone dye.

In particular, the dye is a blond dye, with reflects and shades that can vary from a warm copper tone to a cold golden/chestnut tone, especially on blond hair. Advantageously, in this variant, the exposure time will be less than 1 h, preferably less than 45 minutes.

In particular, the dye is a dark blond dye, with reflects and shades that can vary from dark blond to brown, from a warm copper tone to a cold golden/chestnut tone, especially on blond red or dark blonde hair. Advantageously, in this variant, the exposure time will be less than 1 h, preferably less than 45 minutes.

Alternatively, the cosmetic method for dyeing keratin fibers, notably human, comprises the following steps:

a.1) Providing an extract A according to the invention, optionally with at least one cosmetically-acceptable excipient as defined previously, in particular in dry form, notably in powder form b.1) Preparing an aqueous composition, by adding to the powder of step a.1) an aqueous composition, especially water, at a temperature between 20° C. and 98° C. and mixing c.1) Applying the composition of step b.1) onto keratin fibers, optionally while heating the fibers thus treated d.1) Rinsing a.2) Providing an extract B according to the invention, optionally with at least one cosmetically-acceptable excipient as defined previously, in particular in dry form, notably in powder form b.2) Preparing an aqueous composition, by adding to the powder of step a.2) an aqueous composition, especially water, at a temperature comprised between 20° C. and 98° C. and mixing c.2) Applying the composition of step b.2) to keratin fibers, optionally while heating the fibers thus treated d.2) Rinsing e) Optionally, but not preferably, repeating steps c.1) and d.1) and/or c.2) and d.2). Alternatively, the cosmetic method for dyeing keratin fibers, notably human, comprises the following steps:

a.1) Providing an extract B according to the invention, optionally with at least one cosmetically-acceptable excipient as defined previously, in particular in dry form, notably in powder form b.1) Preparing an aqueous composition, by adding to the powder of step a.1) an aqueous composition, especially water, at a temperature comprised between 20° C. and 98° C. and mixing c.1) Applying the composition of step b.1) onto keratin fibers, optionally while heating the fibers thus treated d.1) Rinsing a.2) Providing an extract A according to the invention, optionally with at least one cosmetically-acceptable excipient as defined previously, in particular in dry form, notably in powder form b.2) Preparing an aqueous composition, by adding to the powder of step a.2) an aqueous composition, especially water, at a temperature comprised between 20° C. and 98° C. and mixing c.2) Applying the composition of step b.2) to keratin fibers, optionally while heating the fibers thus treated d.2) Rinsing e) Optionally, but not preferably, repeating steps c.1) and d.1) and/or c.2) and d.2).

The steps of these two alternatives are advantageously conducted as described previously, with necessary adjustment in view of sequencing.

At either of steps a.1) or a.2), a dyeing agent C according to the invention can also be added, or, alternatively or in addition, a series of steps a.3) to c.3) can be provided, similar to steps a.1) to c.1) but in which the dyeing agent is dyeing agent C.

The present invention also concerns a method for tattooing skin.

The present invention also concerns the use of a dye composition obtained according to the invention as a vegetable ink, for example for printing on paper or cardboard.

The present invention also has for an object a textile dye or furniture stain comprising a composition according to the invention.

Such a dye or stain can also comprise one or more additional dyeing agent(s) or pigment(s). The dye or stain according to the present invention can also comprise any adjuvant known to the skilled person, who knows how to adjust the dye or stain formulation according to the invention using their general knowledge.

The present invention also relates to a use of such a dye or stain for dyeing textile fibers or staining wood fibers.

Thus, the invention also has for an object the use of a composition according to the invention for coloring cellulose materials such as textile fibers, wood fibers, etc.

The following examples illustrate the invention.

FIGURES

CHARACTERIZATION

A) Structural Analyses

Material and Methods

Figure 1:
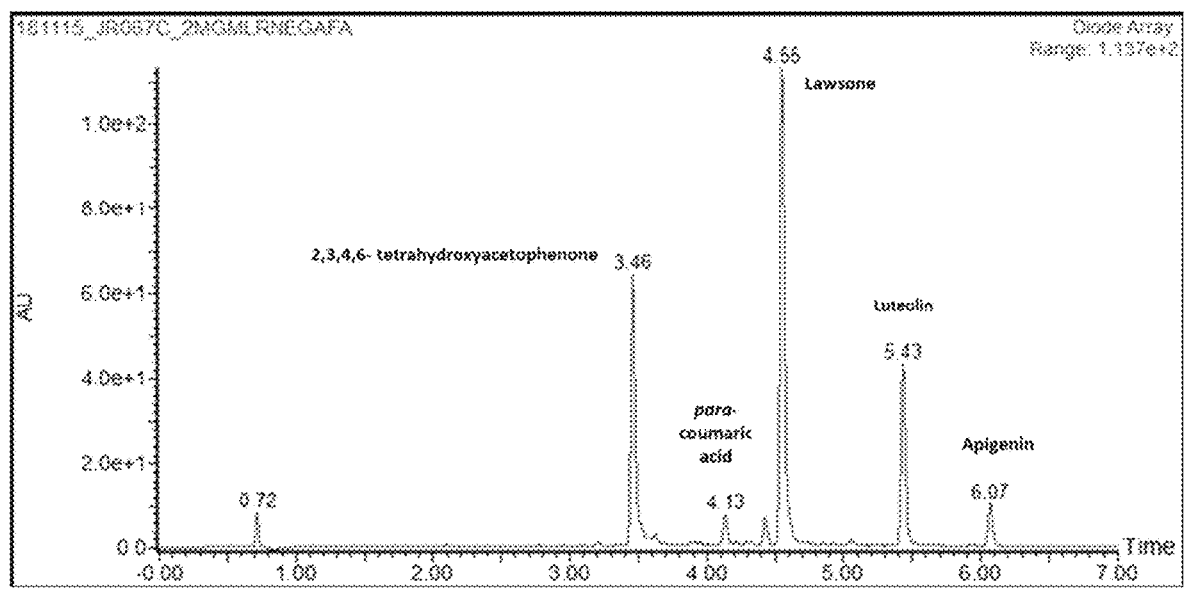
FIG. 1 represents the normalized UHPLC-UV chromatogram of an extract obtained by the process according to example 1.2 (sample E2).

Chromatographic separations were performed on a Waters ACQUITY UHPLC system equipped with a quaternary pump, an auto-sample injector, an on-line degasser, an automatic thermostatic column oven and a DAD detector (200-500 nm). An ACQUITY UPLC BEH Shield RP18 column (100 mm×2.1, 1.7 μm) equipped with a Vanguard™ precolumn (5 mm×2.1) (Waters Corporation, Milford, USA) at 35° C. was used and the flow rate was set at 0.4 mL/min. The mobile phase consisted of a linear gradient system of (A) water with 0.1% formic acid and (B) acetonitrile and (C) methanol as wash solvent: 0-9 min, 2%-100% B; 9-9.55 min, maintain 100% B; 9.55-9.70 min, 0%-100% C; 9.7-10.2 min, maintain 100% C; 10.20-10.35 min, 0%-100% B; 10.35-10.85 min, maintain 100% B; 10.85-11 min, 0%-98% A; held at 98% A—2% B for 1 min for equilibration of the column. Compounds were identified by high-resolution mass spectrometry, 1D- and 2D-NMR experiments (¹H NMR, ¹¹C NMR, DEPT, COSY, HMBC, HSQC).

B) Quantitative Analysis: Experimental Conditions

Luteolin, apigenin were titrated by analytical HPLC performed with a C18 column (XBridge 100 C18; 3.5 mm, 150 mm×4.6 mm) using gradient conditions (see below) with H₂O/trifluoroacetic acid 0.1% (A) and Acetonitrile/trifluoroacetic acid 0.1% (B) as eluent: Gradient conditions: t0 A 18% B 82%; t1 min: A 18% B 82%; 10 min A 50% B 50%; 10.1 min: A 18% B 82%

UV detection is at 340 nm for apigenin and 310 nm for luteolin. Flow rate was 1 mL/min and temperature 40° C. Pure luteolin, apigenin and p-coumarin were used for calibration.

Example 1: Synthesis of Extract A

Example 1.1: Isopropyl Acetate Extract According to the Invention 50 g of uncrushed leaves of *Lawsonia inermis* are extracted by 500 mL of water at 30-40° C. for 30 min. 600 mL of isopropyl acetate are added to this solution. This is mixed for 30 min. After decantation, the upper isopropyl acetate phase (480 mL) is recovered, the aqueous phase being separated because it is practically free of lawsone. The isopropyl acetate phase is filtered then dried with the Rotavapor. The residue is the dry henna extract.

The plant contains 1.5 g of lawsone/100 g of dry plant.

The isopropyl acetate upper phase contains 80.7% of the lawsone potential present in the plant.

The dry henna extract contains 30.2% by weight of lawsone, i.e. 71% of the lawsone present in the plant.

Stability study: sample stored at 25° C., 60% relative humidity and protected from light:

At T0: lawsone content=30.2% by weight of lawsone relative to the weight of the dry extract.

At T1 month: lawsone content=29.7% by weight of lawsone relative to the weight of the dry extract; so no significant loss within the meaning of the present invention.

Example 1.2: Isopropyl Acetate Extract No 2 According to the Invention 49.5 g of uncrushed leaves of *Lawsonia inermis* are extracted by 500 mL of water at 30-40° C. for 30 min. 600 mL of isopropyl acetate are added to this solution. This is mixed for 30 min. After decantation, the upper isopropyl acetate phase is recovered and filtered on Büchner (K900), and the residue is rinsed with 50 mL of isopropyl acetate. The resulting solution is then dried with the Rotavapor. The residue is the dry henna extract (sample E2). The dry henna extract (sample E2) contains 30.9 wt. % of lawsone.

Results

UHPLC-UV Chromatogram

Figure 2:
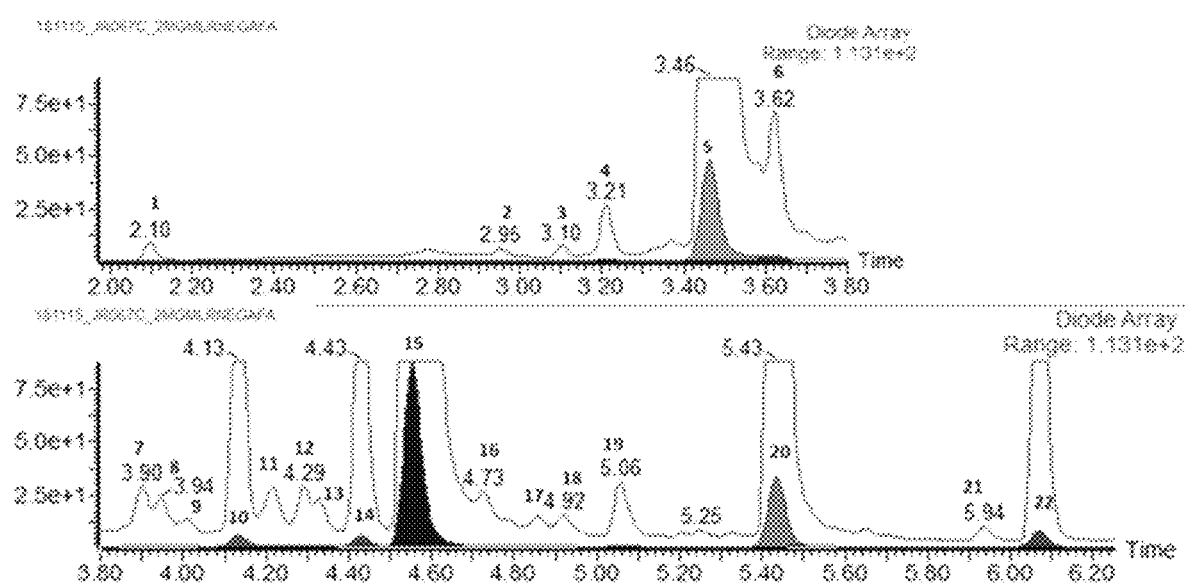
FIG. 2 represents the same chromatogram as in FIG. 1: the filled peaks correspond to the ones that can be seen in FIG. 1, while the plain line corresponds to a zoom of said chromatogram.
Figure 3A:
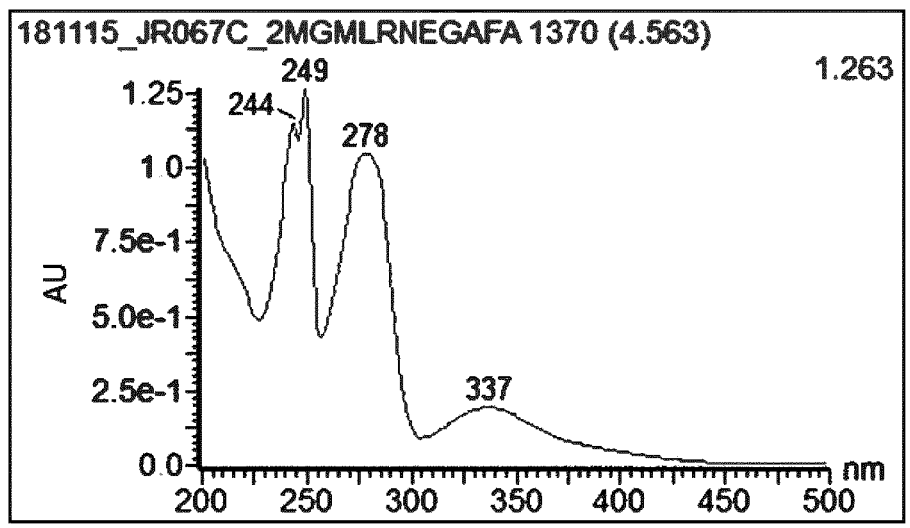
FIGS. 3a, 3b, 3c, 3d and 3e represent the UV spectra of lawson, luteolin, apigenin, para-coumaric acid and 2,3,4,6-tetrahydroxyacetophenone, isolated from sample E2.
Figure 3B:
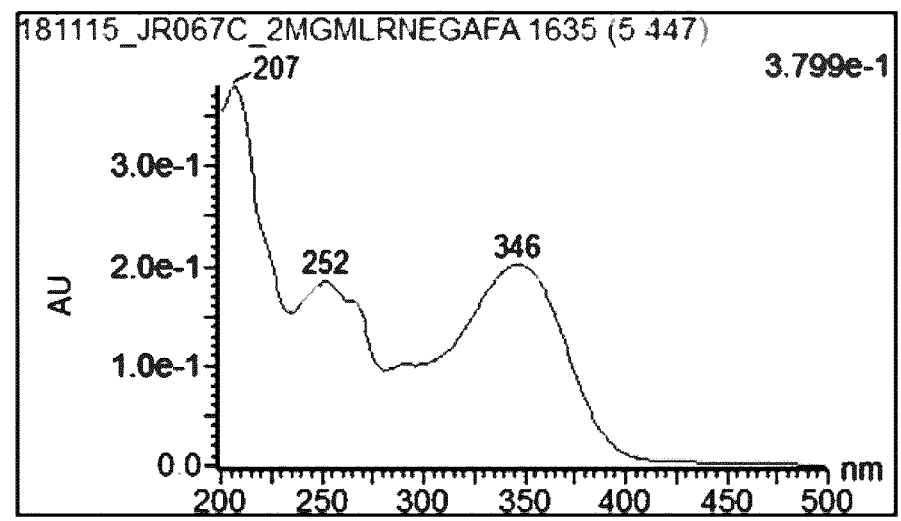
Figure 3C:
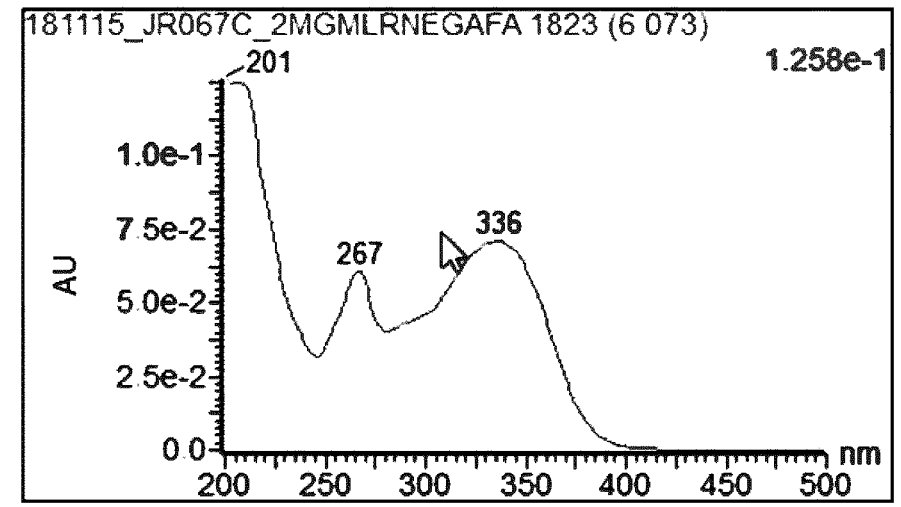
Figure 3D:
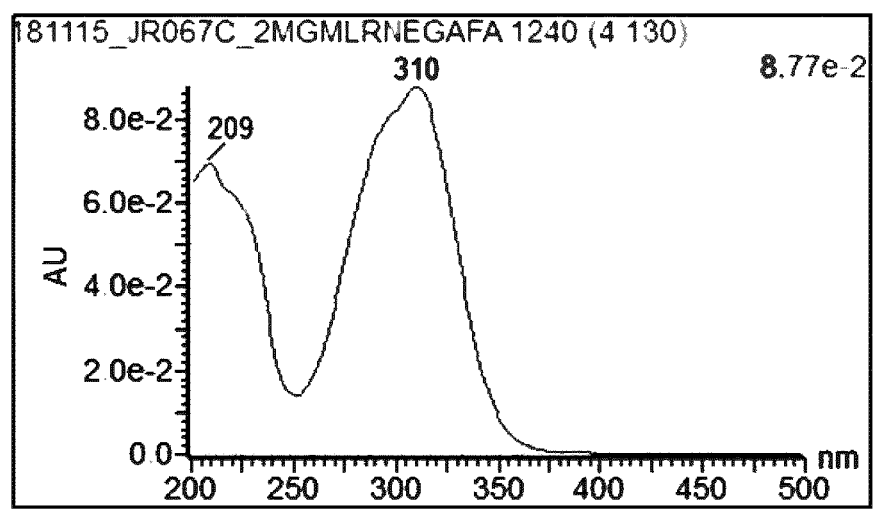
Figure 3E:
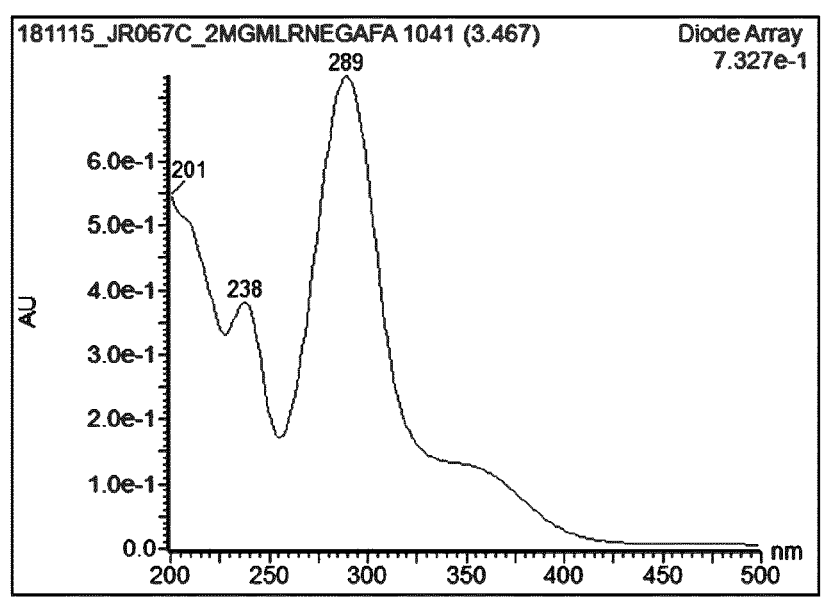
Figure 4A:
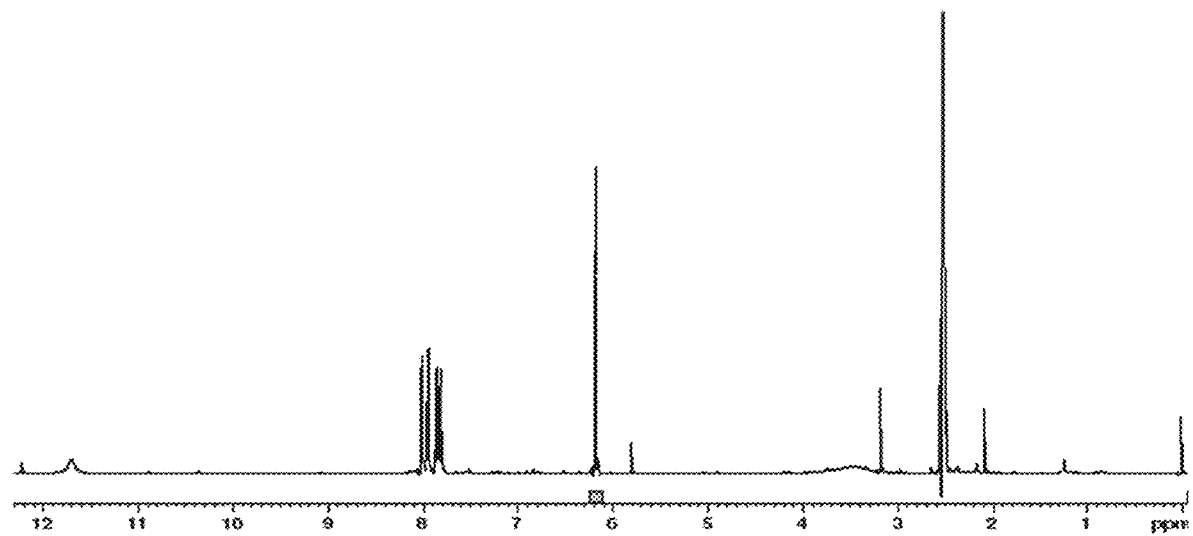
FIG. 4 represents the normalized UHPLC-UV chromatogram of an extract obtained by the process according to example 1.4.
Figure 4B:
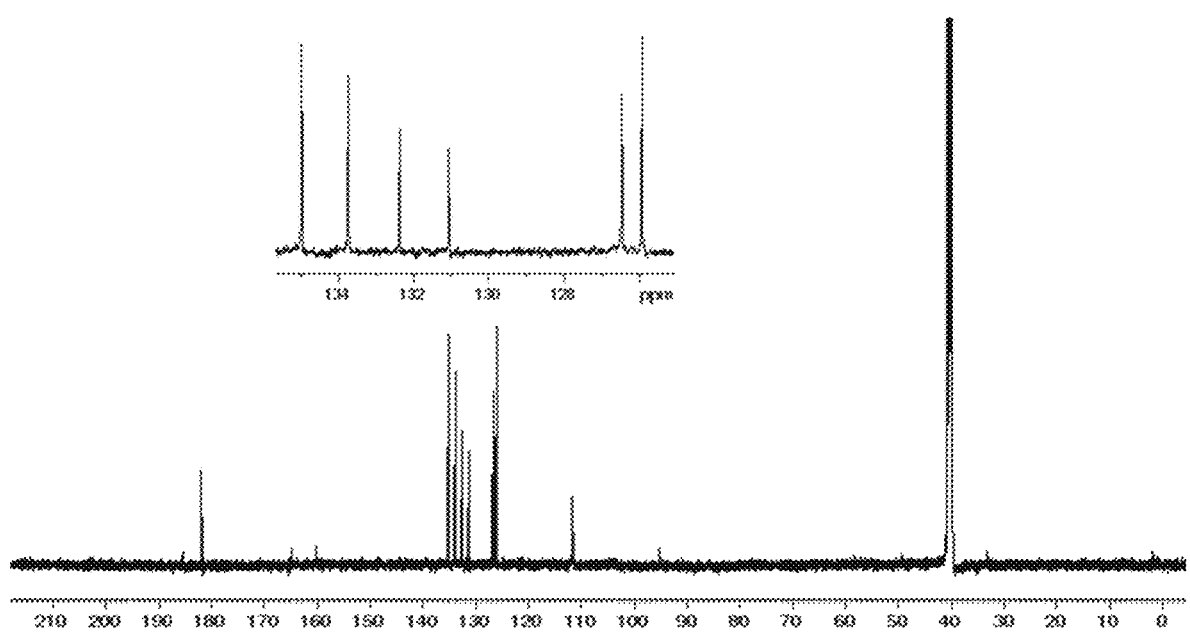
Figure 4C:
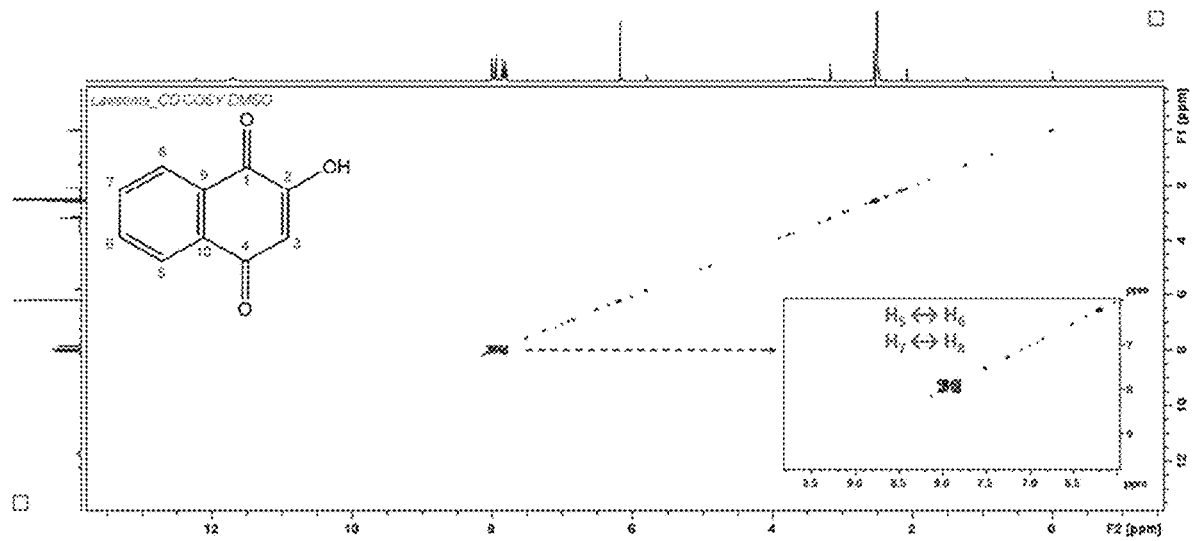
Figure 4D:
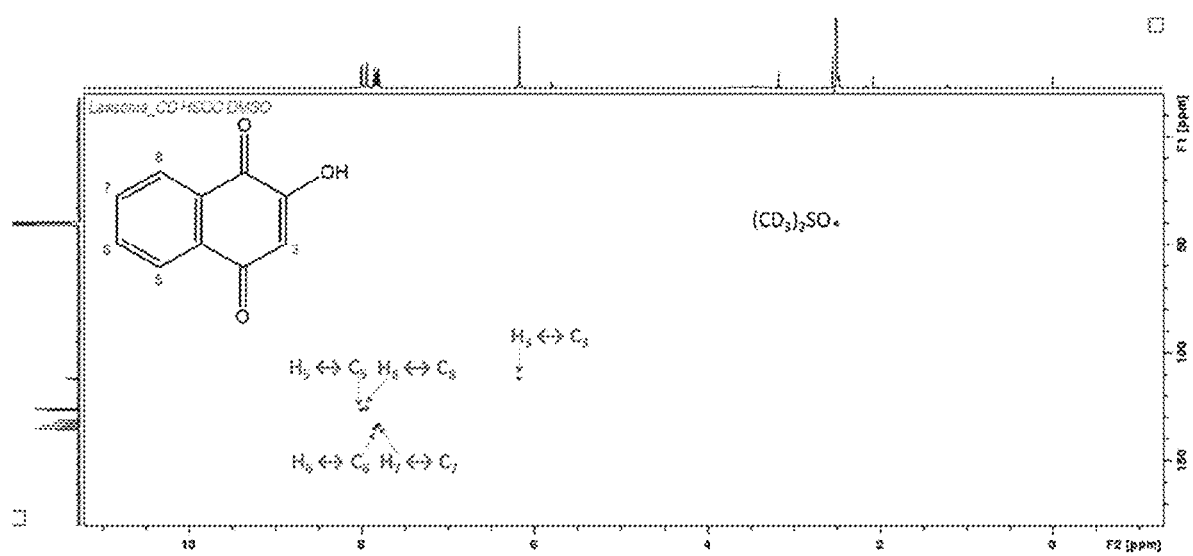
Figure 4E:
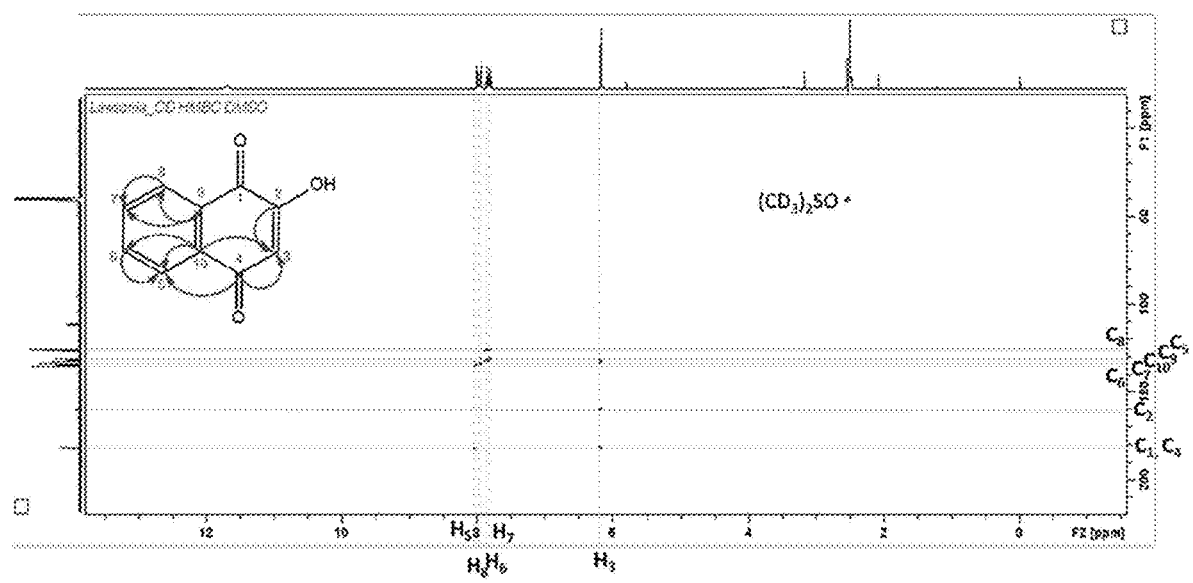

The obtained UHPLC-UV chromatogram is displayed in FIGS. 1 and 2. The peaks that can be observed on a zoom of said chromatogram (FIG. 2, plain line) have been associated with the following compounds:

| 1 | 2 |
|---|---|
| gallic acid | lalioside |
| 3 | 4 |
| myrciaphenone A | catechin |

15
lawsone

| 5 | 6 |
|---|---|
| 2,3,4,6-tetrahydroxyacetophenone | 1,2-dihydroxy-4-O-glycosyloxynaphtalene |
| 7 | 10 |
| luteolin-4'-O-glucoside | para-coumaric acid |
| 11 | 12 |
| apigenin-7-O-β-glucoside | luteolin-3'-O-glucoside |
| 13 | 14 |
| apigenin-4'-O-β-glucoside | 3,4,5-trihydroxyacetophenone |
| 19 | 20 |
| 3',4',5,7-tetrahydroxyflavanone | luteolin |
| 21 | 22 |
| 3',5,7-trihydroxy-4'-methylflavone | apigenin |

UV Spectra

The UV spectra of the compounds corresponding to peaks No 15, 20, 22, 10 and 5 are displayed in FIGS. 3a, 3b, 3c, 3d and 3e respectively.

B) Quantitative Analysis

Material and Methods

Batches Samples

LP110: Henna extract AN, Ethyl acetate extract standardized with maltodextrine—industrial scale.

ES310: Henna extract AN, Ethyl acetate extract standardized with maltodextrine—laboratory scale.

JQ137A: Henna extract AN, Isopropyl acetate Henna extract with fructose—laboratory scale.

The lawsone in each of the above standardized extract is equal to 1.1 wt. %.

Results:

| Sample | Mass (mg) | Vol (mL) | $V_{inj}$ (µg) | $Q_{inj}$(µg) luteolin | apigenin | P-coumaric acid |
|---|---|---|---|---|---|---|
| LP110 1 | 215.5 | 20 | 5 | 0.0951 | 0.0132 | 0.0234 |
| LP110 2 | 266.1 | 20 | 5 | 0.1191 | 0.0163 | 0.0281 |
| LP110 3 | 233.1 | 20 | 5 | 0.1029 | 0.0157 | 0.0256 |
| ES3310 4 | 265.8 | 20 | 5 | 0.2348 | 0.0484 | 0.0285 |
| ES3310 5 | 217.25 | 20 | 5 | 0.195 | 0.0285 | 0.0238 |
| ES3310 6 | 227 | 20 | 5 | 0.2376 | 0.0307 | 0.0262 |
| JQ137A 7 | 235.9 | 20 | 5 | 0.1015 | 0.0178 | 0.0159 |
| JQ137A 8 | 222.6 | 20 | 5 | 0.1039 | 0.0188 | 0.0161 |
| JQ137A 9 | 227.7 | 20 | 5 | 0.1158 | 0.0195 | 0.0176 |

| Extract | Mean content (wt. %) | | |
|---|---|---|---|
| | luteolin | apigenin | p-coumaric acid |
| LP110 | 0.18% | 0.03% | 0.04% |
| ES3310 | 0.38% | 0.06% | 0.04% |
| JQ137A | 0.19% | 0.03% | 0.03% |

Example 1.3: Ethyl Acetate Standardized Dry Extract According to the Invention 50 g of crushed leaves of *Lawsonia inermis* are extracted by 500 mL of water at 30-40° C. for 30 min. 600 mL of ethyl acetate are added to this solution. This is mixed for 30 min. After decantation, the upper ethyl acetate phase is recovered and the aqueous phase is removed because of its very low lawsone content.

The lawsone content of the ethyl acetate phase is determined by H.P.L.C, and maltodextrin is added in sufficient quantity to obtain a mixture containing 1.3 wt % of lawsone, which is then lyophilized.

The dry henna extract standardized with maltodextrin contains 1.1 wt. % of lawsone, i.e. 71% of the initial lawsone content in the plant.

Example 1.4: n-Butanol Extract According to the Invention 50 g of uncrushed leaves of *Lawsonia inermis* are extracted by 6 volumes of water at 30-40° C. for 30 min. Six volumes of n-butanol are added to this solution at room temperature. This mixture is stirred for 30 min. After decantation, the upper butanol phase is recovered, the aqueous phase being removed because it is practically free of lawsone. The organic phase is concentrated with passage over water.

The lawsone content in the n-butanol phase is determined by HPLC. Maltodextrin is added in an amount sufficient to obtain a mixture comprising from 1.1 to 1.3 wt. % of lawsone.

The concentrate is dried to obtain a powder.

Results

UHPLC-UV Chromatogram

Figure 5:
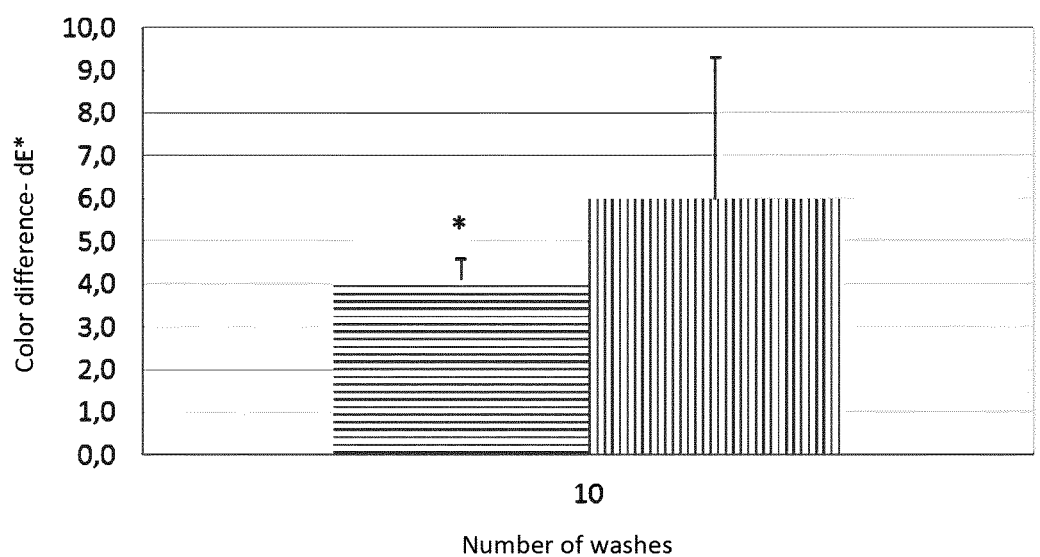
FIG. 5 represents color difference dE* after 10 washes for product I1 (vertical lines) or for control T1 (horizontal lines)

The obtained UHPLC-UV chromatogram is displayed in FIG. 5. The peaks that can be observed have been associated with the following compounds:

| Resolution time | Compound |
| --- | --- |
| 4.47 | lawsone |
| 3.38 | 2,3,4,6-tetrahydroxyacetophenone |
| 5.34 | luteolin |
| 5.96 | apigenin |

The presence of glycosylated luteolin, in particular of luteolin-6-C-neohesperidoside and coumaric acid, is noted.

Example 2: Synthesis of Extract B

Example 2.1

Crushed *Lawsonia inermis* leaves are introduced into a 50-g reactor with 6 volumes of water. The paste obtained is stirred for 30 min at 50° C. Then add 16 volumes of ethanol to this mixture, i.e. a final alcohol content of 80% v/v, then shake vigorously for 30 min. The entire paste is filtered (on an AF15 filter) and the hydroalcoholic filtrate is recovered, sterilized and then concentrated by evaporation of ethanol. The aqueous concentrate is then dried. The dry product corresponds to the dry henna extract (yield by weight: 54%).

The extract thus obtained comprises (% expressed in weight relative to the total weight of the dry extract):
lawsone 0.6%;
saccharide compounds: 69.9% (total sugars) (polysaccharides content 59.3%);
apigenin 0.05%;
luteolin 0.17%.

Example 2.2

Crushed *Lawsonia inermis* leaves are introduced into a 50-g reactor with 6 volumes of water. The paste obtained is stirred for 30 min at 50° C. Stir vigorously for an additional 30 min. The entire paste is filtered (on an AF15 filter) and the aqueous filtrate is recovered, sterilized 20 min at 120° C. and then concentrated. The aqueous concentrate is then dried. The dry product corresponds to the dry henna extract (yield by weight: 60%).

The extract thus obtained comprises 0.4% of lawsone,% expressed in weight relative to the total weight of the dry extract.

Example 3: Comparison of the Characteristic Compounds of Extracts A and B

The characteristic compounds of the extracts obtained according to Example 1 or according to Example 2 are reported in the following table; the percents are expressed by weight relative to the total weight of the dry extract:

TABLE 5

| Compounds | Standardized extract AN (Example 1) | Extract B (Example 2) |
| --- | --- | --- |
| Lawsone | 1-1.3 | <0.6 |
| Phenol compounds | 0.2-3 | >15 |
| Tannins | n.d. | n.m. |
| luteolin | 0.05-1 | 0.1-0.3 |
| Apigenin | 0.01-0.5 | 0.05-0.5 |
| Para-coumaric acid | 0.01-0.1 | n.m. |
| 2,3,4,6-tetrahydroxyacetophenone | 0.05-1 | 0.02-0.1 |
| Gallic acid | n.m. | 0.1-0.3 |
| 3,4,5-trihydroxyacetophenone | n.m. | n.d. |
| 1,3,6.7-trihydroxyacetophenone | n.d. | n.m. |
| Saccharide compounds | <0.5 | 70-75 |
| Malic acid, succinic acid, ascorbic acid | n.d. | 4-5 | n.d. means not detected, so the compound was not detected during analysis n.m. means not measured, so the compound was detected during analysis but was not measured

Example 4: Assessment of the Color Retention on White, Natural Human Hair Strands after Washing An extract A according to the invention (that of Example 1.2) is mixed with an extract B according to the invention (that of Example 2.2) in a B/A weight ratio of 1/1. This mixture is designated product I1. A conventional henna powder is also used (finely crushed *Lawsonia inermis* leaves (<250 μm)) as a control. This powder is called product T1.

In each case, 10 g of powder are mixed with 40 g of water before application onto the strand. The two products I1 and T1 were assessed for their dye content following washing. All the strands underwent standardized washes up to 10 times with a neutral shampoo.

For each product I1 and T1, the color of 5 natural white human hair test strands, color 10 (white) was measured using a reflectance colorimeter (CR400 Croma Meter, Minolta, France). The color parameters measured by this device, L*a*b*, describe the strand colors. The parameter assessed is a derivative of L*a*b, i.e., the color difference (dE*).

$$dE^* = \sqrt{((L_1^* - L_2^*)^2 + (a_2^* - a_1^*)^2 + (b_2^* - b_1^*)^2)} \qquad \text{[Math 1]}$$

Where $L_1^*$, $a_1^*$, $b_1^*$ are the coordinates in the CIELAB color space established in 1976 by the International Commission on Illumination of the first color to be compared and $L_2^*$, $a_2^*$, $b_2^*$ those of the second.

In our case, the "1" values are the Lab values of the dyed strands before washing, and the "2" values the values obtained after 10 washes.

Statistical study concluded that the color difference with the combination according to the invention I1 is significantly less than the control T1 (*p<0,05).

The results are reported in FIG. 5.

Method 1: Lawsone Assay by HPLC

This method can be applied for:
A. the assay of lawsone in an extract
B. the assay of the total lawsone present in the free form or form of glycosylated lawsone derivatives in the aerial parts of *Lawsonia inermis*, obtained by acid hydrolysis, and thus quantifying the lawsone potential in the plant,
C. the assay of the lawsone formed by enzymes.

Reagents

Lawsone>97% (HPLC) SIGMA—ref: H46805
Dichloromethane for analyses.
Sulfuric acid for analyses.
Methanol for analyses.
HPLC-grade water.
HPLC-grade acetonitrile.
HPLC-grade trifluoroacetic acid.

HPLC Conditions

Column: XBridge C18, 3.5 µm, 4.6×150 mm Waters
Furnace: 40° C.
Solvents: S-A: 0.1% trifluoroacetic acid in water.
S-B: 0.1% trifluoroacetic acid in acetonitrile.
Gradient: T0 min 40% S-A; T 1 min 40% S-A; T 10 min 5% S-A; T 11 min 5%
S-A; T 11.1 min 40% S-A.
Wavelength: λ=278 nm.
Flow rate: 1 mL/min
Injection: 10 µL.

Sample Preparation:

For whole or roughly crushed leaves:
50 g of leaves are crushed then sieved through a 0.355 µm sieve.

For leaf powders:

Use 50 g of leaf powder as is.

Preparation of the Solutions

Control solutions:

Lawsone solution at 0.3 mg/mL in 1/1 methanol/ethanol. Dilute to 1/10, 1/20, 1/100 in 1/1 methanol/water.

Test solutions:

Test solution A (assay of the lawsone present in an extract)
Dissolve 50 mg of extract in 100 mL of 1/1 methanol/water. Dissolve with ultrasound. Filtration on Acrodisc GFGHP. Inject 10 µL.

Test solution B (assay of total lawsone)
Introduce 80 mg of leaf powder into a volumetric flask. Add 50 mL of 2N $H_2SO_4$. Heat to 97° C. for 30 min. Let cool. Add methanol qs 100 mL. Filter the solution on Acrodisc GF GHP 0.45 µm. Inject 10 µL of the filtrate.

Test solution C (assay of the lawsone formed by enzymes)
Introduce 80 mg of leaf powder into a volumetric flask. Add into 50 mL of demineralized water. Place in an ultrasound bath for 30 min between 30 and 40° C. Let cool. Add methanol qs 100 mL. Filter the solution on Acrodisc GF GHP 0.45 µm. Inject 10 µL of the filtrate.

Results

Use the regression line calculated with the control solutions to determine:
A. the lawsone content of the extract,
B. the total lawsone content, and/or
C. the content in lawsone formed by the enzymes.

Method 2: Assay of Nitrogen-Containing Compounds (Amino Acids, Proteins

Free amino acids and proteins can be assayed before or after hydrolysis by ninhydrin spectrophotometry. The results are expressed in percentage of amino acids relative to asparagine.

Assay of Total Proteins and Amino Acids

Principle

Colorimetric assay of amino acids by the ninhydrin reagent after acid hydrolysis. The results are expressed in percentage of total amino acids relative to asparagine.

Reagents

Citrate buffer (pH=5)
Dissolve 2.1 g of citric acid in 20 mL of water, add 20 mL of 1 N sodium hydroxide and adjust to 50 mL with water.

Ninhydrin reagent:
Dissolve 0.08 g of tin (II) chloride ($SnCl_2$, $2H_2O$) in 50 ml of citrate buffer (pH=5).
Dissolve 2 g of ninhydrin in 50 mL ethylene glycol monomethyl ether (EGME).
Mix the two solutions.

6N hydrochloric acid
Dilute to 1/2 of concentrated hydrochloric acid (36%).

Diluent
Mix 100 mL of 1-propanol with 100 mL of water.

Preparation of the Solutions

Preparation of the calibration range
Dissolve 17 mg of asparagine in 100 mL of water.

Preparation of the test solutions
Weigh approximately 30 to 200 mg of extract depending on the sample to analyze ($pe_1$) in a screw thread tube, add 2 mL of 6N HCl.
Hermetically seal then place for around 16 hours at 110° C.
Neutralize with 3N sodium hydroxide (methyl red changes color) then adjust to 20 ml with water.

Assay

|  | T 0.1 | T 0.2 | T 0.5 | Test | Blank |
|---|---|---|---|---|---|
| Control solution (mL) | 0.1 | 0.2 | 0.5 | — | — |
| Test solution (mL) | — | — | — | 0.2 | — |
| Water (mL) | 1 | 1 | 1 | 1 | 1 |
| Ninhydrin reagent (mL) | 1 | 1 | 1 | 1 | 1 |

Stir and place in a water bath at 100° C. for 20 minutes. Cool in an ice bath. Adjust to 10 ml with diluent.
Measure the absorbance at 570 nm of the different solutions against the blank.

Calculations

Construct the calibration curve. Deduce from it the total amino acid concentration ($Q_{AAT}$), expressed in asparagine, in the test solutions. The total amino acid content ($T_{AAT}$) of the extract is given by the following formula:

$$T_{AAT}(\%) = \frac{Q_{AAT} \times 100 \times 20}{pe_1}$$

with $Q_{AAT}$ in mg/ml et $pe_1$ in mg

Method 3: Weight Assay of Chlorophylls

The chlorophyll content in the extract may be evaluated by the weight obtained after washing the extract with heptane. The extract is taken up by 10 volumes of methanol.

After stirring for 15 min, the solution is filtered. The supernatant is dried and constitutes the fraction containing chlorophylls.

Method 4: Spectrophotometric Assay of Phenol Compounds

The content of phenol compounds in the extract can be evaluated by spectrophotometry according to the method of the European Pharmacopoeia, version 9.0, 2.8.14.

The solutions to be tested are prepared by dissolving 25 mg of extract in 100 mL of water. The content of phenol compounds is expressed by reference to pyrogallol.

Method 5: Colorimetric Assay of Saccharide Compounds Before and After Hydrolysis Principle: Colorimetric determination of saccharide compounds by dinitrosalicylic acid (DNS) compared to glucose before and after hydrolysis. The results are expressed as the percentage of saccharide compounds relative to glucose.

Reagents:

DNS reagents: dissolve 30 g of sodium and potassium ditartrate in 50 ml of water. Add 20 mL of 2N sodium hydroxide. Dissolve 1 g of dinitrosalicylic acid (DNS) while slightly heating. Make up to 100 mL with water.

Preparation of Solutions:

Preparation of the calibration range: dissolve 5 mg of glucose in 10 mL of water.

Preparation of hydrolyzed test solutions (total saccharide compounds): Weigh about 1 g of extract (pe2). Add 1 mL of 4N H2SO4. Heat at reflux for 2 hours. Neutralize with 1N sodium hydroxide and transfer to a 20 mL volumetric flask. Make up to 20 mL with water.

Preparation of non-hydrolyzed test solutions (free saccharide compounds=monosaccharides): weight about 10 g of extract (pe3) in a 20 mL volumetric flask. Make up to 20 mL with water.

Dosage: the solutions are dosed according to the following table:

|  | T 0.5 | T1 | T1.5 | T2 | Tests | Blank |
| --- | --- | --- | --- | --- | --- | --- |
| Control solution (ml) | 0.5 | 1 | 1.5 | 2 | — | — |
| Test solution (ml) | — | — | — | — | 1 | — |
| Water (ml) | 1.5 | 1 | 0.5 | 0 | 1 | 2 |
| DNS | 1 | 1 | 1 | 1 | 1 | 1 |

Shake and then place for 5 minutes in a water bath at 100° C. Cool on an ice bath and make up to 10 mL with water. Measure the absorbance at 540 nm of the different solutions against the blank.

Calculation:

Construct the calibration curve.

Deduce the concentration of total saccharide compounds (QSRT) and free saccharides (QSRL), expressed as glucose, in the test solutions. The titer in total saccharide compounds (TSRT) of the extract is provided by the following formula:

$$T_{SRT}(\%) = \frac{Q_{SRT} \times 100 \times 20}{pe_2}$$

With $Q_{SRT}$ in mg/ml and $pe_2$ in mg

The titer in free saccharide compounds (TSRL) of the extract is provided by the following formula:

$$T_{SRL}(\%) = \frac{Q_{SRL} \times 100 \times 20}{pe_3}$$

With $Q_{SRL}$ in mg/ml and $pe_3$ in mg

Method 6: HPLC Assay of Organic Acids

Principle: HPLC assay of the organic acids from a plant extract. The organic acids assayed are: succinic, malic and ascorbic acids.

Chromatographic System:

Column: Atlantis dc18 5 µm 5 µm 250×4.6 mm Waters or equivalent;

Temperature: 25° C.;

Mobile phase: Solvent A: 50 mM phosphate buffer, pH 2.8; Solvent B: Acetonitrile;

Gradient: T0% A: 100%; 7.5 min % A: 100%; 15 min % A: 90%; 16 min % A: 50%; 23 min % A: 50%; 24 min % A: 100%; 40 min % A: 100%;

Flow rate: 1 mL/min;

λ=200 at 400 nm (extraction at 214 nm);

Injection volume: 5 µL.

Preparation of the Solutions:

Control solution: Weigh 10 mg of control and dissolve in 20 mL of purified water. Carry out the dilutions to 1/5, 1/10 and 1/20.

Test solution: Weigh 250 mg of substance to be analyzed in a 20-mL volumetric flask. Fill with water—Run through ultrasound if necessary.

Results: The chromatograms of the control and test solutions have several characteristic and identical peaks.

The retention time of the controls are:

Malic acid 5.5 min,

Ascorbic acid: 7.7 min,

Ascorbic acid: 11.7 min.

Draw the calibration curve for each of controls and deduce the quantity of the sample.

The invention claimed is:

1. A method for preparing a dye composition comprising the following steps:
providing an extract A of the aerial parts of *Lawsonia inermis* containing from 7 to 60% by weight of lawsone relative to the total weight of the dry extract, wherein the lawsone results notably from enzymatic hydrolysis of glycosylated lawsone derivatives; and
providing an extract B of the aerial parts of *Lawsonia inermis* containing less than 0.6% by weight of lawsone, at least 15% by weight of phenol compounds and at least 60% by weight of saccharide compounds, including polysaccharides, relative to the total weight of the dry extract;
mixing extract A and extract B;
obtaining a dye composition.

2. The method according to claim 1 wherein extract A of the aerial parts of *Lawsonia inermis* further comprises luteolin, apigenin and 2,3,4,6-tetrahydroxyacetophenone.

3. The method according to claim 1 wherein the extract A of the aerial parts of *Lawsonia inermis* further comprises coumaric acid.

4. The method according to claim 1 wherein the extract A of the aerial parts of *Lawsonia inermis* does not contain more than 2% by weight of proteins, peptides or amino acids relative to the total weight of the dry extract.

5. The method according to claim 1 wherein the dye composition comprises a standardized dry extract AN of *Lawsonia inermis* which comprises the extract A of the aerial parts of *Lawsonia inermis* and a carrier, the standardized dry extract AN comprising from 0.6 to 1.4% by weight of lawsone relative to the total weight of the standardized dry extract.

6. The method according to claim 5, wherein the standardized dry extract AN of *Lawsonia inermis* comprises, relative to the total weight of the dry extract:
- from 0.05 to 1.0% by weight of luteolin;
- from 0.01 to 0.5% by weight of apigenin;
- from 0.01 to 1.0% by weight of 2,3,4,6-tetrahydroxyacetophenone.

7. The method according to claim 1 wherein the extract A of the aerial parts of *Lawsonia inermis* is obtained by a process comprising the following steps:
- a) macerating the aerial parts of *Lawsonia inermis* in water, at a pH ranging from 4 to 8, in order for the glycosylated lawsone derivatives initially present in the aerial parts of *Lawsonia inermis* to be partially or totally hydrolyzed enzymatically, to provide an aqueous solution containing lawsone;
- b) adding an organic solvent to the solution obtained from step a), the organic solvent being chosen from $C_4$-$C_{12}$ linear, or branched, alcohols or solvents having a miscibility with water which is less than 10% by weight at 25° C., to provide an aqueous phase and an organic phase;
- c) recovering the organic phase obtained from step b); and
- d) concentrating the organic phase recovered from step c), to provide an extract A as recited in claim 1.

8. The method according to claim 7 wherein step a) is performed according to at least one of the following conditions:
- step a) is conducted at a temperature ranging from 20° C. to 60° C.;
- step a) is conducted at a pH ranging from 5 to 7.5;
- step (a) is performed under stirring for 15 min to 2 h;
- step (a) is conducted in a volume of water whose weight is 2 to 15 times greater than the weight of the aerial parts of *Lawsonia inermis* subjected to maceration.

9. The method according to claim 1 wherein the saccharide compounds of extract B further comprise monosaccharides, disaccharides and combinations thereof.

10. The method according to claim 1 wherein the extract B further comprises from 2 to 8% by weight of organic acids related to the total weight of the dry extract B.

11. The method according to claim 1 wherein the phenol compounds of extract B are selected from the group consisting of:
- gallic acid, coumaric acid, and/or heterosides of such compounds and combinations thereof;
- tannins,
- phloroglucinol derivatives; and
- flavonoid derivatives.

12. The method according to claim 1 wherein extract B is an aqueous, hydroalcoholic or alcoholic extract of *Lawsonia inermis*.

13. The method according to claim 1 wherein the extract A is mixed with extract B according to a B/A weight ratio greater than or equal to 1, the extract A being a standardized dry extract.

14. The method according to claim 1 wherein the extract A is mixed with extract B according to a B/A weight ratio less than 1, the extract A being a standardized dry extract.

15. A dye composition obtained by the method according to claim 1.

16. The dye composition according to claim 15 further comprising one or more cosmetically-acceptable excipients suitable for application on human keratin fibers.

17. A cosmetic method for dyeing human keratin fibers comprising the following steps:
- a) providing a composition according to claim 15 in powder form,
- b) preparing an aqueous composition, by adding to the powder of step a) an aqueous composition at a temperature between 20° C. and 98° C. and mixing,
- c) applying onto keratin fibers, optionally while heating the fibers thus treated,
- d) rinsing,
- e) optionally, repeating steps c) and d).

* * * * *